(12) United States Patent
Yamane et al.

(10) Patent No.: US 12,365,870 B2
(45) Date of Patent: Jul. 22, 2025

(54) STORAGE STABILIZER FOR EXTRACELLULAR VESICLE AND STORAGE STABILIZATION METHOD FOR EXTRACELLULAR VESICLE

(71) Applicant: FUJIFILM Wako Pure Chemical Corporation, Osaka (JP)

(72) Inventors: Masayuki Yamane, Amagasaki (JP); Naoko Imawaka, Amagasaki (JP); Yuji Nakagawa, Osaka (JP); Kodai Sasamoto, Amagasaki (JP)

(73) Assignee: FUJIFILM Corporation, Tokyo (JP)

( * ) Notice: Subject to any disclaimer, the term of this patent is extended or adjusted under 35 U.S.C. 154(b) by 769 days.

(21) Appl. No.: 17/504,067

(22) Filed: Oct. 18, 2021

(65) Prior Publication Data

US 2022/0033765 A1 Feb. 3, 2022

Related U.S. Application Data

(63) Continuation of application No. PCT/JP2020/016738, filed on Apr. 16, 2020.

(30) Foreign Application Priority Data

Apr. 19, 2019 (JP) .................................. 2019-080005

(51) Int. Cl.
*C12N 5/00* (2006.01)
*C08F 126/10* (2006.01)

(52) U.S. Cl.
CPC .............. *C12N 5/00* (2013.01); *C08F 126/10* (2013.01)

(58) Field of Classification Search
CPC .................................................... C08F 126/10
See application file for complete search history.

(56) References Cited

U.S. PATENT DOCUMENTS 5,178,884 A * 1/1993 Goodrich ............... A61K 35/18
424/533
5,876,754 A * 3/1999 Wunderlich ............ A61K 8/65
514/773

(Continued)

FOREIGN PATENT DOCUMENTS

CN 101287449 A 10/2008
CN 104208677 A 12/2014

(Continued)

OTHER PUBLICATIONS

Alberro, A.; Iparraguirre, L.; Fernandes, A.; Otaegui, D. Int. J. Mol. Sci. 2021, 22, 8163. (Year: 2021).*

(Continued)

*Primary Examiner* — Michael F Pepitone
(74) *Attorney, Agent, or Firm* — Sughrue Mion, PLLC

(57) ABSTRACT

An object of the present invention is to provide a means capable of stably storing an extracellular vesicle. The present invention relates to a storage stabilizer for an extracellular vesicle, which contains a copolymer containing a monomer unit derived from vinylpyrrolidone and a monomer unit derived from vinyl acetate, or a polymer having a monomer unit derived from vinylpyrrolidone such as polyvinylpyrrolidone and relates to a storage stabilization method for an extracellular vesicle, which includes cryopreserving an extracellular vesicle in the presence of the polymer.

9 Claims, 14 Drawing Sheets

(56) References Cited

U.S. PATENT DOCUMENTS

| | | | |
|---|---|---|---|
| 2003/0215515 | A1 | 11/2003 | Truong-Le et al. |
| 2006/0127375 | A1* | 6/2006 | Livesey .................. A01N 1/02 |
| | | | 435/2 |
| 2009/0155331 | A1* | 6/2009 | Ruddy .................. A61P 25/24 |
| | | | 977/773 |
| 2012/0252795 | A1* | 10/2012 | Nguyen .................. A61P 3/06 |
| | | | 514/347 |
| 2015/0125864 | A1 | 5/2015 | Kang et al. |
| 2019/0275159 | A1 | 9/2019 | Soane et al. |
| 2023/0247982 | A1* | 8/2023 | Joseph ................ A01N 1/0226 |
| | | | 435/2 |

FOREIGN PATENT DOCUMENTS

| | | | | |
|---|---|---|---|---|
| CN | 109355258 | A | 2/2019 | |
| EP | 2253306 | A1 * | 11/2010 | ........... A61K 9/0053 |
| JP | 2006-512102 | A | 4/2006 | |
| JP | 2018-130085 | A | 8/2018 | |
| KR | 10-2010-0112206 | A | 10/2010 | |
| WO | 03/087335 | A2 | 10/2003 | |
| WO | 2018/070939 | A1 | 4/2018 | |
| WO | 2020/257710 | A1 | 12/2020 | |

OTHER PUBLICATIONS

Ashland Product Grades (Year: 2020).*
Extended European Search Report dated Dec. 23, 2022 in European patent application No. 20792189.1.
Chi-Gu Kim et al., "Effect of the Polyvinylpyrrolidone Concentration of Cryoprotectant on Mouse Embryo Development and Production of Pups: 7.5% of PVP is Beneficial for In Vitro and In Vivo Development of Frozen-Thawed Mouse Embryos", Journal of Reproduction and Development, 2008, vol. 54, No. 4, pp. 250-253 (4 pages total).
S.S. Ray et al., "Serum-free non-toxic freezing solution for cryopreservation of human adipose tissue-derived mesenchymal stem cells", Biotechnol Lett, 2016, vol. 38 No. 8, pp. 1397-1404 (8 pages total).
International Search Report issued Jul. 14, 2020 in International Application No. PCT/JP2020/016738.
Written Opinion of the International Searching Authority issued Jul. 14, 2020 in International Application No. PCT/JP2020/016738.
International Preliminary Report on Patentability issued Sep. 28, 2021 in International Application No. PCT/JP2020/016738.
Thirumala et al., "Evaluation of Polyvinylpyrrolidone as a Cryoprotectant for Adipose Tissue-Derived Adult Stem Cells", Tissue Engineering: Part C, 2010, vol. 16, No. 4, pp. 783-792 (10 pages total).
Fuhrmann et al., "Stability of extracellular vesicles during lyophilization—implications for their pharmaceutical use", Journal of Extracellular Vesicles, 2016, vol. 5, No. 30924, p. 14, Poster 27 (2 pages total).
Ahmed et al., "Formulation and clinical investigation of optimized vinopocetine lyoplant-tabs: new strategy in development of buccal solid dosage form", Drug Design, Development and Therapy, 2019, vol. 13, pp. 205-220 (16 pages total).
Souzu, "Mechanism of defect and protection by freezing of living cells", Kagaku To Seibutsu, 1980, vol. 18, No. 2, pp. 78-87 (10 pages total).
Dai-Ichi Kogyo Seiyaku Shaho, "Water soluble polymers in aqueous solution, Unique water-soluble polymer, polyvinylpyrrolidone", 2016, No. 576, p. 17 (1 page total).
Bosch et al., "Trehalose prevents aggregation of exosomes and cryodamage", Scientific Reports, vol. 6, No. 36162, pp. 1-11 (2016)(11 pages total).
Office Action issued May 23, 2023 in Japanese Application No. 2021-514217.
Office Action issued Mar. 10, 2023 in Australian Application No. 2020259891.
Communication dated Dec. 16, 2023 issued by the State Intellectual Property Office of the P.R.China in Chinese application No. 202080029711.5.
Communication dated Nov. 3, 2023 issued by the Taiwanese Patent Office in Taiwanese application No. 109113011.
Volker Bühler, "Kollidon®: Polyvinylpyrrolidone excipients for the pharmaceutical industry", 9th revised edition, Mar. 2008, pp. 4-330 (331 pages total), https://www.pharmacompass.com/pAssets/pdf/edgm/application/gmp-kollidon.pdf.
Office Action issued Jul. 14, 2023 in Chinese Application No. 202080029711.5.
Office Action issued May 22, 2024 in Korean Application No. 10-2021-7035069.

* cited by examiner

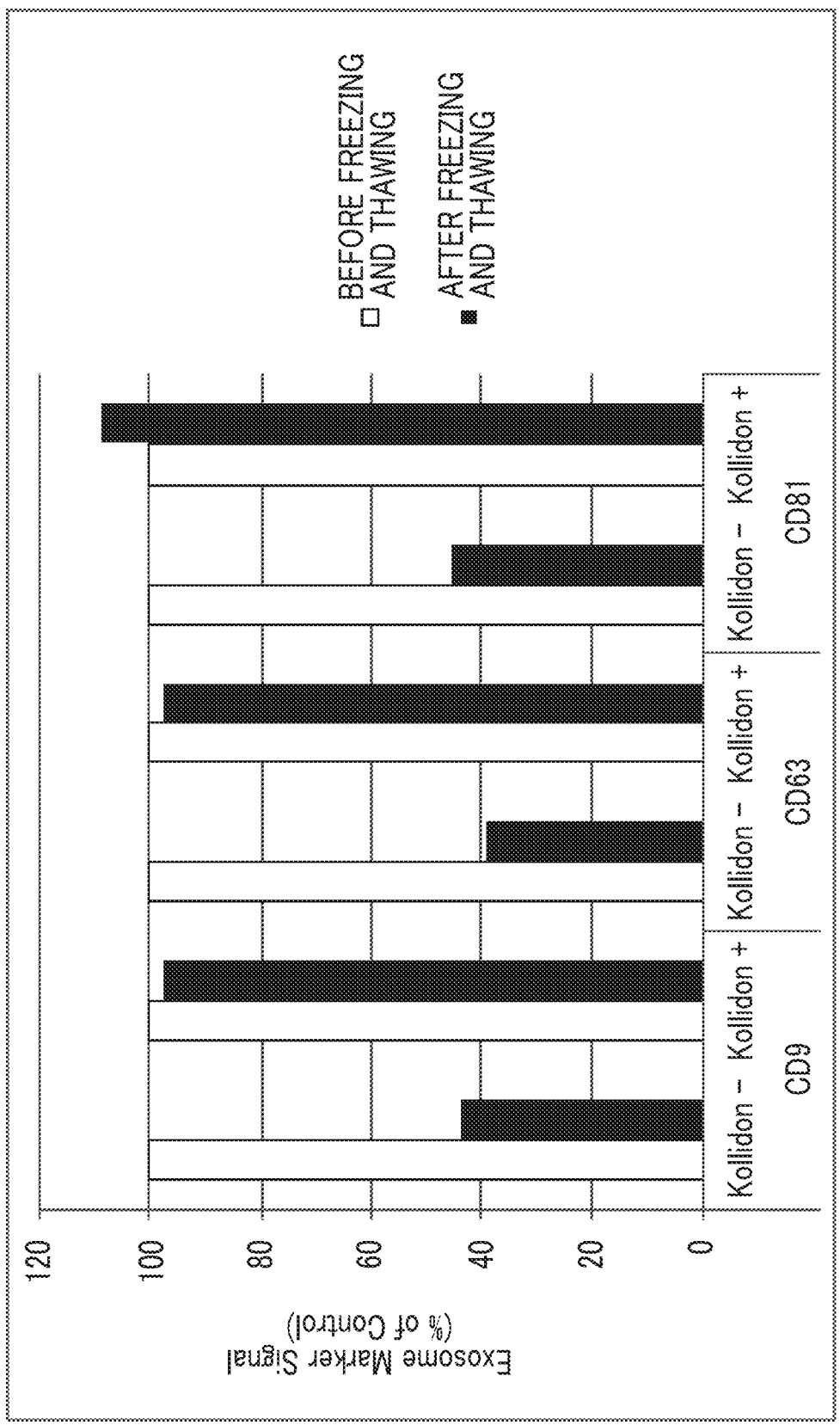

FIG. 9
0 TIMES
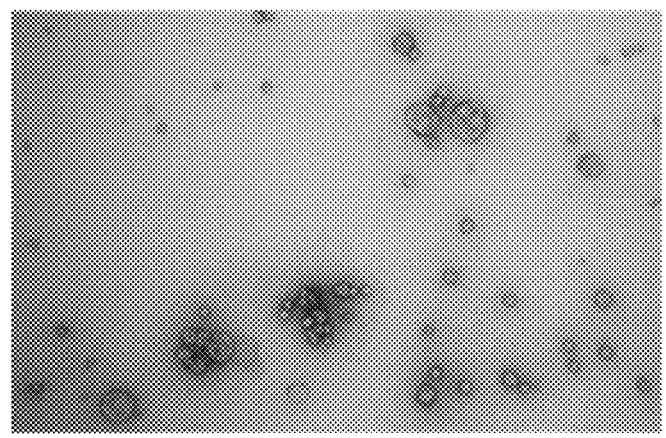
15 TIMES
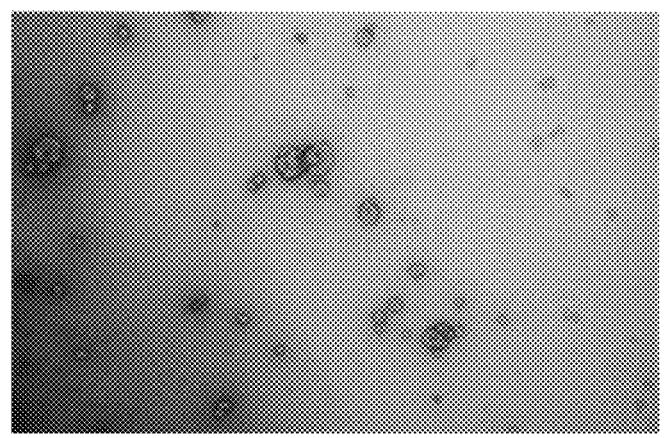

STORAGE STABILIZER FOR EXTRACELLULAR VESICLE AND STORAGE STABILIZATION METHOD FOR EXTRACELLULAR VESICLE

CROSS-REFERENCE TO RELATED APPLICATIONS

This application is a Continuation of PCT International Application No. PCT/JP2020/016738, filed on Apr. 16, 2020, which claims priority under 35 U.S.C. § 119(a) to Japanese Patent Application No. 2019-080005, filed on Apr. 19, 2019. Each of the above application(s) is hereby expressly incorporated by reference, in its entirety, into the present application.

TECHNICAL FIELD

The present invention relates to a storage stabilizer for an extracellular vesicle and a storage stabilization method for an extracellular vesicle.

BACKGROUND ART

It is known that proteins and nucleic acids such as microRNAs are present inside of an extracellular vesicle particle, and the extracellular vesicle is responsible for substance transfer between cells. Extracellular vesicles are also secreted into body fluids such as blood, and proteins and microRNAs in the extracellular vesicles are attracting attention as diagnostic markers for diseases. Furthermore, since it has been shown that exosomes derived from some stem cells have a tissue repair ability and are useful as a delivery tool for nucleic acid drugs, they are also expected to be applicable to a pharmaceutical product.

In a case of using an extracellular vesicle as a diagnostic marker or a pharmaceutical product as described above or in a case of carrying out basic research such as a functional analysis of an extracellular vesicle, it is necessary to store the extracellular vesicle without deteriorating the quality thereof. For this reason, cryopreservation is general as the storage of the extracellular vesicle.

In addition, it is known that trehalose is used for cryopreservation of an extracellular vesicle (Non-Patent Literature 1).

CITATION LIST

Non-Patent Literature

[Non-Patent Literature 1] Steffi Bosch, Laurence de Beaurepaire, Marie Allard, Mathilde Mosser, Claire Heichette, Denis Chretien, Dominique Jegou & Jean-Marie Bach. Trehalose prevents aggregation of exosomes and cryodamage. Scientific Reports volume 6, Article number: 36162 (2016)

SUMMARY OF INVENTION

Technical Problem

Extracellular vesicles are susceptible to freezing, and repeated freezing and thawing operations may reduce the number of extracellular vesicle particles.

An object of the present invention is to provide a means capable of stably storing an extracellular vesicle.

Solution to Problem

In order to achieve the object, the inventors of the present invention have diligently examined whether an extracellular vesicle could be stably stored by using various compounds and, as a result of the examinations, have found that an extracellular vesicle can be stably stored by storing the extracellular vesicle in the presence of a polymer having a monomer unit derived from vinylpyrrolidone.

The present invention relates to a storage stabilizer for an extracellular vesicle and a storage stabilization method for an extracellular vesicle.

[1] A storage stabilizer for an extracellular vesicle, comprising a polymer having a monomer unit derived from vinylpyrrolidone.

[2] The storage stabilizer according to [1], in which the polymer is a copolymer containing a monomer unit derived from vinylpyrrolidone and a monomer unit derived from vinyl acetate, or is polyvinylpyrrolidone.

[3] The storage stabilizer according to [1], in which the polymer is a copolymer containing a monomer unit derived from vinylpyrrolidone and a monomer unit derived from vinyl acetate.

[4] The storage stabilizer according to [2] or [3], in which a constitution ratio of the monomer unit derived from vinylpyrrolidone to the monomer unit derived from vinyl acetate in the copolymer is 1:0.1 to 1:3.

[5] The storage stabilizer according to any one of [2] to [4], in which a Fikentscher K value of the copolymer is 5 to 50.

[6] The storage stabilizer according to any one of [2] to [5], in which a weight-average molecular weight of the copolymer is 3,000 to 250,000.

[7] The storage stabilizer according to [1], in which the polymer is polyvinylpyrrolidone.

[8] The storage stabilizer according to [2] or [7], in which a Fikentscher K value of the polyvinylpyrrolidone is 5 to 140.

[9] The storage stabilizer according to any one selected from [2], [7], or [8], in which a weight-average molecular weight of the polyvinylpyrrolidone is 1,000 to 3,000,000.

[10] A storage stabilization method for an extracellular vesicle, comprising cryopreserving an extracellular vesicle in a presence of a polymer having a monomer unit derived from vinylpyrrolidone.

[11] The storage stabilization method for an extracellular vesicle according to [10], in which the polymer is a copolymer containing a monomer unit derived from vinylpyrrolidone and a monomer unit derived from vinyl acetate, or is polyvinylpyrrolidone.

[12] The storage stabilization method for an extracellular vesicle according to [10], in which the polymer is a copolymer containing a monomer unit derived from vinylpyrrolidone and a monomer unit derived from vinyl acetate.

[13] The storage stabilization method for an extracellular vesicle according to [11] or [12], in which a constitution ratio of the monomer unit derived from vinylpyrrolidone to the monomer unit derived from vinyl acetate in the copolymer is 1:0.1 to 1:3.

[14] The storage stabilization method for an extracellular vesicle according to any one of [11] to [13], in which a Fikentscher K value of the copolymer is 5 to 50.

[15] The storage stabilization method for an extracellular vesicle according to any one of [11] to [14], in which a weight-average molecular weight of the copolymer is 3,000 to 250,000.

[16] The storage stabilization method for an extracellular vesicle according to [10], in which the polymer is polyvinylpyrrolidone.

[17] The storage stabilization method for an extracellular vesicle according to [11] or [16], in which a Fikentscher K value of the polyvinylpyrrolidone is 5 to 140.

[18] The storage stabilization method for an extracellular vesicle according to any one selected from [11], [16], or [17], in which a weight-average molecular weight of the polyvinylpyrrolidone is 1,000 to 3,000,000.

Advantageous Effects of Invention

According to the storage stabilizer for an extracellular vesicle of the present invention and the storage stabilization method for an extracellular vesicle of the present invention, it is possible to stably stored an extracellular vesicle.

BRIEF DESCRIPTION OF DRAWINGS

FIG. 1A is a graph showing results of exosome storage stabilization tests using Kollidon (registered trade name) VA64, which are obtained from Example 1 and Comparative Example 1.

FIG. 9 shows images which show results of verifying effects of the number of times of freezing and thawing operation on the storage stabilization of exosomes with electron microscopic observation, which are obtained from Example 6.

DESCRIPTION OF EMBODIMENTS

Figure 1B:
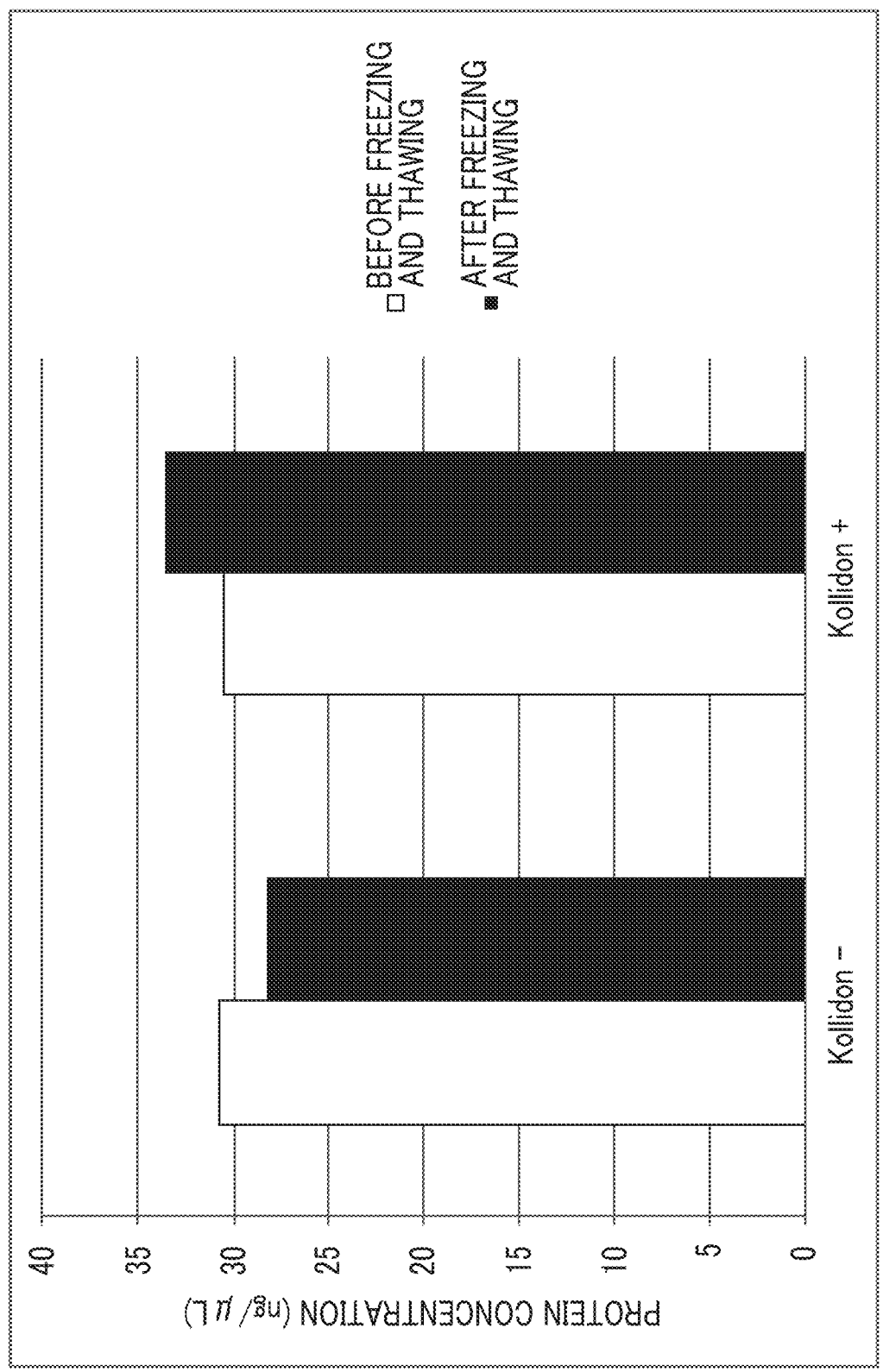
FIG. 1B is a graph showing results of verifying changes in protein concentration before and after an exosome storage stabilization test, which are obtained from Experimental Example 1 and Experimental Example 2.

Storage stabilization according to an embodiment of the present invention means making storage of an extracellular vesicle possible in a state of maintaining physiological activity thereof. Specific examples thereof include reducing adverse effects on the physiological activity of the extracellular vesicle due to cryopreserving the extracellular vesicle. Examples of the adverse effects include a decrease in the number of particles of extracellular vesicle and, loss of activity of a lipid constituting an extracellular vesicle or a protein present on the surface of the membrane thereof, or loss of activity of a protein, a peptide, a nucleic acid, or the like, contained in an extracellular vesicle, due to undergoing denaturation by external factors such as the temperature during storage or undergoing temporal change.

The physiological activity of the extracellular vesicle can be checked by, for example, measuring the activity of marker proteins present on the membrane surface of the extracellular vesicle, such as CD9, CD63, and CD81, measuring the number of extracellular vesicle particles with a nano tracking analysis (NTA) method, observing the number of extracellular vesicle particles and the state such as the shape thereof with an electronmicroscope, and measuring the number of proteins and peptides with the proteome analysis.

Storage Stabilizer for Extracellular Vesicle of Present Invention

A storage stabilizer (hereinafter, may be abbreviated as a storage stabilizer according to the embodiment of the present invention) for an extracellular vesicle according to the embodiment of the present invention is a storage stabilizer for an extracellular vesicle, which contains a polymer having a monomer unit derived from vinylpyrrolidone. According to the storage stabilizer according to the embodiment of the present invention, it is possible to stably cryopreserve an extracellular vesicle.

A polymer (hereinafter, may be abbreviated as a polymer according to the embodiment of the present invention) that is used for the storage stabilizer according to the embodiment of the present invention may be a homopolymer (polyvinylpyrrolidone) or may be a copolymer as long as the polymer has a monomer unit derived from vinylpyrrolidone. Examples of the copolymer include a copolymer containing a monomer unit derived from vinylpyrrolidone and a monomer unit derived from vinyl acetate, and a copolymer consisting of only a monomer unit derived from vinylpyrrolidone and a monomer unit derived from vinyl acetate is more preferable.

Due to having a high effect of stabilizing an extracellular vesicle, the polymer according to the embodiment of the present invention is preferably a copolymer containing a monomer unit derived from vinylpyrrolidone and a monomer unit derived from vinyl acetate, and more preferably a copolymer consisting of only a monomer unit derived from vinylpyrrolidone and a monomer unit derived from vinyl acetate. In addition, as the polymer according to the embodiment of the present invention, polyvinylpyrrolidone is useful since it is used as a bioacceptable material.

One kind of the polymer according to the embodiment of the present invention, such as those described above, may be used alone, or two or more kinds thereof may be mixedly used, and it is preferably used alone. It should be noted that a polymer containing a constitutional unit that is added in association with a polymerization reaction, such as a structure derived from a polymerization initiator, is also contained the polymer according to the embodiment of the present invention. That is, a homopolymer (polyvinylpyrrolidone) or a copolymer consisting of only a monomer unit derived from vinylpyrrolidone and a monomer unit derived from vinyl acetate consist of only these two monomer units as the monomer unit; however, it may contain a constitutional unit other than the monomer unit that is added in association with a polymerization reaction, such as a structure derived from a polymerization initiator.

The Fikentscher K value of the polymer according to the embodiment of the present invention is not particularly limited; however, it is, for example, 5 to 140, preferably 6 to 100, and more preferably 7 to 40. The Fikentscher K value is a viscosity characteristic value that correlates with the molecular weight, and is a numerical value calculated by applying a relative viscosity value (25° C.) measured by a capillary viscometer to a Fikentscher expression (1) below.

$$K = \frac{1.5 \log \eta_{rel} - 1}{0.15 + 0.003c} + \frac{[300c \log \eta_{rel} + (c + 1.5c \log \eta_{rel})^2]^{1/2}}{0.15c + 0.003c^2} \quad (1)$$

In the expression (1), ηrel is a relative viscosity of a polymer aqueous solution with respect to water, and c is a polymer concentration (%[w/v]) in a polymer aqueous solution.

The weight-average molecular weight of the polymer according to the embodiment of the present invention is not particularly limited; however, it is, for example, 1,000 to 3,000,000, preferably 1,000 to 2,000,000, and more preferably 1,000 to 150,000.

The constitution ratio of the monomer unit derived from vinylpyrrolidone to the monomer unit derived from vinyl acetate in the copolymer is not particularly limited; however, it is, for example, 1:0.1 to 1:3, preferably 1:0.2 to 1:2, more preferably 1:0.3 to 1:1, and still more preferably 1:0.4 to 1:1.

The Fikentscher K value of the copolymer is not particularly limited; however, it is, for example, 5 to 50, preferably 10 to 45, more preferably 15 to 40, and still more preferably 20 to 40.

The weight-average molecular weight of the copolymer is not particularly limited; however, it is, for example, 3,000 to 250,000, preferably 5,000 to 200,000, more preferably 10,000 to 150,000, still more preferably 20,000 to 100,000, and particularly preferably 30,000 to 80,000.

Examples of the copolymer include a copolymer in which the constitution ratio of the monomer unit derived from vinylpyrrolidone to the monomer unit derived from vinyl acetate is 1:0.1 to 1:3, where the Fikentscher K value of the copolymer is 5 to 50 or/and the weight-average molecular weight thereof is 3,000 to 250,000. The copolymer is preferably a copolymer in which the constitution ratio of the monomer unit derived from vinylpyrrolidone to the monomer unit derived from vinyl acetate is 1:0.2 to 1:2, where the Fikentscher K value of the copolymer is 10 to 45 or/and the weight-average molecular weight thereof is 5,000 to 200,000, more preferably a copolymer in which the constitution ratio of the monomer unit derived from vinylpyrrolidone to the monomer unit derived from vinyl acetate is 1:0.3 to 1:1, where the Fikentscher K value of the copolymer is 15 to 40 or/and the weight-average molecular weight thereof is 10,000 to 150,000, still more preferably a copolymer in which the constitution ratio of the monomer unit derived from vinylpyrrolidone to the monomer unit derived from vinyl acetate is 1:0.4 to 1:1, where the Fikentscher K value of the copolymer is 20 to 40 or/and the weight-average molecular weight thereof is 20,000 to 100,000, and particularly preferably a copolymer in which the constitution ratio of the monomer unit derived from vinylpyrrolidone to the monomer unit derived from vinyl acetate is 1:0.4 to 1:1, where the Fikentscher K value of the copolymer is 20 to 40 or/and the weight-average molecular weight thereof is 30,000 to 80,000.

Examples of the copolymer include Kollidon (registered trade name) VA64 (manufactured by BASF SE) in which the constitution ratio of the monomer unit derived from vinylpyrrolidone to the monomer unit derived from vinyl acetate is 6:4. The Fikentscher K value of Kollidon (registered trade name) VA64 is 25.2 to 30.8, and the weight-average molecular weight thereof is 45,000 to 70,000.

The Fikentscher K value of the polyvinylpyrrolidone is not particularly limited; however, it is, for example, 5 to 140, preferably 6 to 100, more preferably 7 to 40, still more preferably 8 to 30, and particularly preferably 9 to 20.

The weight-average molecular weight of the polyvinylpyrrolidone is not particularly limited; however, it is, for example, 1,000 to 3,000,000, preferably 1,000 to 2,000,000, more preferably 1,000 to 100,000, still more preferably 1,000 to 40,000, and particularly preferably 1,500 to 15,000.

Examples of polyvinylpyrrolidone include a polyvinylpyrrolidone in which the Fikentscher K value is 5 to 140 and the weight-average molecular weight is 1,000 to 3,000,000. The polyvinylpyrrolidone is preferably a polyvinylpyrrolidone in which the Fikentscher K value is 6 to 100 and the weight-average molecular weight is 1,000 to 2,000,000, more preferably a polyvinylpyrrolidone in which the Fikentscher K value is 7 to 40 and the weight-average molecular weight is 1,000 to 100,000, still more preferably a polyvinylpyrrolidone in which the Fikentscher K value is 8 to 30 and the weight-average molecular weight is 1,000 to 40,000, and particularly preferably a polyvinylpyrrolidone in which the Fikentscher K value is 9 to 20 and the weight-average molecular weight is 1,500 to 15,000.

Examples of the polyvinylpyrrolidone include Kollidon (registered trade name) 12PF (molecular weight: 2,000 to 3,000, K value: 10.2 to 13.8), Kollidon (registered trade name) 17PF (molecular weight: 7,000 to 11,000, K value: 15.3 to 18.0), Kollidon (registered trade name) 25 (molecular weight: 28,000 to 34,000, K value: 22.5 to 27.0), Kollidon (registered trade name) 30 (molecular weight: 44,000 to 54,000, K value: 27.0 to 32.4), Kollidon (registered trade name) 90F (molecular weight: 1,000,000 to 1,500,000, K value: 81.0 to 96.3), and PVP K-120 (molecular weight: 2,100,000 to 3,000,000, K value: 110 to 130). The polyvinylpyrrolidone is preferably Kollidon (registered trade name) 12PF, Kollidon (registered trade name) 17PF, Kollidon (registered trade name) 25, Kollidon (registered trade name) 30, or Kollidon (registered trade name) 90F, more preferably Kollidon (registered trade name) 12PF, Kollidon (registered trade name) 17PF, Kollidon (registered trade name) 25, or Kollidon (registered trade name) 30, still more preferably Kollidon (registered trade name) 12PF, Kollidon (registered trade name) 17PF, or Kollidon (registered trade name) 25, and particularly preferably Kollidon (registered trade name) 12PF, Kollidon (registered trade name) 17PF.

The storage stabilizer according to the embodiment of the present invention may contain an aqueous solvent in addition to the polymer according to the embodiment of the present invention. Examples of the aqueous solvent include water; a buffer solution such as a phosphate buffer solution, a carbon dioxide buffer solution, or a Good's buffer solution (for example, a HEPES buffer solution, a Tris buffer solution, or an IVIES buffer solution); and physiological saline. In addition, the aqueous solvent may further contain substances that are used in the related field, such as a sensitizing agent, a surfactant, an antiseptic (for example, sodium azide, salicylic acid, benzoic acid, or the like), a stabilizer (for example, albumin, globulin, water-soluble gelatin, a surfactant, a saccharide, or the like), and an activation agent, where the substances do not inhibit the stability of the polymer according to the embodiment of the present invention or the extracellular vesicle according to the embodiment of the present invention or do not inhibit the storage stabilization effect of the extracellular vesicle, which is exhibited by the polymer according to the embodiment of the present invention, and the concentration range and the like of the substances, which are generally used in the related field, may be appropriately selected and used.

The concentration of the polymer according to the embodiment of the present invention in the storage stabilizer according to the embodiment of the present invention is generally 0.005% to 20% (w/v), preferably 0.01% to 15% (w/v), and more preferably 0.05% to 10% (w/v).

The pH of the storage stabilizer according to the embodiment of the present invention is generally 5 to 10, preferably 5.5 to 9.5, and more preferably 5 to 9.

Extracellular Vesicle According to Present Invention

The extracellular vesicle according to the embodiment of the present invention is a small membrane vesicle composed of a lipid bilayer, which is derived from a cell. The extracellular vesicle generally has a diameter of 20 nm to 1,000 nm, preferably 50 nm to 800 nm, more preferably 50 nm to 500 nm, and particularly preferably 50 nm to 200 nm. Examples of the extracellular vesicle according to the embodiment of the present invention include those classified variously according to the generation origin thereof and the size of the small membrane vesicle as described in Nature Reviews Immunology 9, 581-593 (August 2009) and "Obesity Research" Vol. 13 No. 2, 2007, Topics, Naoto Aoki et al. Specific examples thereof include an exosome, a microvesicle, an ectosome, a membrane particle, an exosome-like vesicle, an apoptotic body, and an adiposome.

Among these, the storage stabilizer according to the embodiment of the present invention is more useful for an exosome and a microvesicle, and it is particularly useful for an exosome.

The exosome is a small membrane vesicle composed of a lipid bilayer, which is derived from a cell, and examples thereof include an exosome having a diameter of 50 nm to 200 nm. An exosome of 50 nm to 150 nm is preferable, and an exosome of 50 nm to 100 nm is more preferable. It should be noted that an exosome is conceived to be derived from a late endosome.

The microvesicle is a small membrane vesicle composed of a lipid bilayer, which is derived from a cell, and examples thereof include a microvesicle having a diameter of 100 nm to 1,000 nm. A microvesicle having a diameter of 100 nm to 800 nm is preferable, and a microvesicle having a diameter of 100 nm to 500 nm is more preferable. It should be noted that the microvesicle is conceived to be derived from the cell membrane.

The extracellular vesicle according to the embodiment of the present invention may be contained in a biological specimen or may be isolated from a biological specimen, and an extracellular vesicle isolated from a biological specimen is preferable.

The biological specimen is not particularly limited as long as it can contain the extracellular vesicle according to the embodiment of the present invention. Examples of the biological specimen include a body fluid specimen, a cell culture supernatant, and a cell extract, and a body fluid specimen or a cell culture supernatant is preferable. Examples of the body fluid specimen include blood-derived specimens such as blood, serum, and plasma, and body fluid specimens that are used in the field of clinical examination, such as urine, buffy coat, saliva, semen, chest exudate, cerebrospinal fluid, tears, sputum, mucus, lymph, ascites, pleural effusion, amniotic fluid, bladder lavage fluid, and bronchoalveolar lavage fluid, and blood-derived specimens are preferable. Examples of the cell culture supernatant include a culture supernatant obtained by culturing, according to a conventional method, a COLO201 cell, an MM1 cell, a BLCL21 cell, a U87 MG cell, an SK-N-SH cell, an HCT116 cell, a PC3 cell, a BPH-1 cell, a DAUDI cell, an A549 cell, a K562 cell, an iPS cell, a mesenchymal stem cell (MSC), a fibroblast, an umbilical vein endothelial cell, a T cell, a macrophage, a B cell, or a dendritic cell. Examples of the cell extract include an extract obtained by carrying out disruption, according to a conventional method, to extract a COLO201 cell, an MM1 cell, a BLCL21 cell, a U87 MG cell, an SK-N-SH cell, an HCT116 cell, a PC3 cell, a BPH-1 cell, a DAUDI cell, an A549 cell, a K562 cell, an iPS cell, a mesenchymal stem cell (MSC), a fibroblast, an umbilical vein endothelial cell, a T cell, a macrophage, a B cell, or a dendritic cell.

The biological specimen may be, for example, a biological specimen that has been directly collected from an animal, or may be a biological specimen that has been subjected to pretreatments such as recovery, concentration, purification, isolation, dilution with a buffer solution, and filtration sterilization. These pretreatments may be appropriately carried out according to a conventional method that is used in the related field. The animal is not particularly limited as long as it can contain an extracellular vesicle, and examples thereof include a human, a rat, a mouse, a rabbit, a cow, a goat, a horse, a pig, a dog, a cat, a hamster, a donkey, and a guinea pig, and a human is preferable.

The method for isolating an extracellular vesicle from a biological specimen may be carried out according to a conventional method and is not particularly limited. Examples of the method for isolating an extracellular vesicle from a biological specimen include an affinity method (for example, a PS affinity method), a fractional centrifugation method (for example, an ultracentrifugation method such as a pellet-down method, a sucrose cushion method, or a density gradient centrifugation method, an immunoprecipitation method, chromatography (for example, ion exchange chromatography or gel permeation chromatography), a density gradient method (for example, a sucrose density gradient method), electrophoresis (for example, organelle electrophoresis), a magnetic separation method (for example, magnetically activated cell sorting (MACS) method), an ultrafiltration concentration method (for example, a nanomembrane ultracentrifugation concentration method), a Percoll gradient isolation method, a method using a microfluidic device, and a PEG precipitation method. An affinity method with which an extracellular vesicle having a high degree of purity can be obtained or a fractional centrifugation method that enables theoretically unbiased recovery is preferable, an affinity method or an ultracentrifugation method is more preferable, and an affinity method is particularly preferable. Among the affinity methods, a PS affinity method is preferable. The affinity method and the fractional centrifugation method may be carried out, for example, based on the method described in JP2016-088689A.

One of these isolation methods may be used alone, or two or more methods may be combined. In addition, isolation by one isolation method may be repeated twice or more.

The storage stabilizer according to the embodiment of the present invention is used in a method for storing the extracellular vesicle according to the embodiment of the present invention in the presence of the storage stabilizer according to the embodiment of the present invention. The extracellular vesicle according to the embodiment of the present invention may be stored according to the conventional method for the storage of an extracellular vesicle. According to the storage stabilizer according to the embodiment of the present invention, it is possible to stably store the extracellular vesicle according to the embodiment of the present invention.

Storage Stabilization Method for Extracellular Vesicle of Present Invention

A storage stabilization method (hereinafter, may be abbreviated as a storage stabilization method according to the embodiment of the present invention) for an extracellular vesicle according to the embodiment of the present invention is a storage stabilization method for an extracellular vesicle, which includes cryopreserving an extracellular vesicle in the presence of a polymer (a polymer according to the embodiment of the present invention) having a monomer unit derived from vinylpyrrolidone.

That is, the storage stabilization method according to the embodiment of the present invention is a method of bringing the polymer according to the embodiment of the present invention into contact with an extracellular vesicle and cryopreserving the extracellular vesicle in the presence of the polymer according to the embodiment of the present invention.

Specifically, it is a method of bringing the polymer according to the embodiment of the present invention into contact with an extracellular vesicle to prepare a storage solution (hereinafter, may be abbreviated as a storage solution according to the embodiment of the present invention) containing the polymer according to the embodiment of the present invention and the extracellular vesicle, thereby cryopreserving the storage solution.

The polymer having a monomer unit derived from vinylpyrrolidone in the storage stabilization method according to the embodiment of the present invention is the same as that described in the section of "Storage Stabilizer for Extracellular Vesicle of Present Invention", and the same applies to the specific examples and the preferred one.

In addition, the extracellular vesicle that is used in the storage stabilization method according to the embodiment of the present invention is the same as that described in the section of "Extracellular Vesicle according to Present Invention", and the same applies to the specific examples and the preferred one.

The preparation method for the storage solution according to the embodiment of the present invention is not particularly limited as long as it is a method for finally obtaining a solution containing the polymer according to the embodiment of the present invention and an extracellular vesicle. Specific examples of the preparation method for the storage solution according to the embodiment of the present invention include a method of mixing the storage stabilizer according to the embodiment of the present invention containing an aqueous solvent with a solution containing a biological specimen or an extracellular vesicle, a method of mixing the storage stabilizer according to the embodiment of the present invention containing an aqueous solvent with an extracellular vesicle, and a method of mixing the polymer according to the embodiment of the present invention with a solution containing a biological specimen or an extracellular vesicle. A method of mixing the storage stabilizer according to the embodiment of the present invention containing an aqueous solvent with a solution containing a biological specimen or an extracellular vesicle is preferable.

The storage stabilizer according to the embodiment of the present invention containing the aqueous solvent is the same as that described in the section of "Storage Stabilizer for Extracellular Vesicle of Present Invention", and the same applies to the preferred one.

The solvent in the solution containing the extracellular vesicles is preferably an aqueous solvent. Examples of the aqueous solvent include water; a buffer solution such as a phosphate buffer solution, a carbon dioxide buffer solution, or a Good's buffer solution (for example, a HEPES buffer solution, a Tris buffer solution, or an MES buffer solution); and physiological saline. In addition, the aqueous solvent may further contain substances that are used in the related field, such as a sensitizing agent, a surfactant, an antiseptic (for example, sodium azide, salicylic acid, benzoic acid, or the like), a stabilizer (for example, albumin, globulin, water-soluble gelatin, a surfactant, a saccharide, or the like), and an activation agent, where the substances do not inhibit the stability of the polymer according to the embodiment of the present invention or the extracellular vesicle according to the embodiment of the present invention or do not inhibit the storage stabilization effect of the extracellular vesicle, which is exhibited by the polymer according to the embodiment of the present invention, and the concentration range and the like of the substances, which are generally used in the related field, may be appropriately selected and used.

The pH of the solution containing the extracellular vesicles is generally 5 to 10, preferably 5.5 to 9.5, and more preferably 5 to 9.

The concentration of the polymer according to the embodiment of the present invention in the storage solution according to the embodiment of the present invention is not particularly limited; however, it is, for example, 0.0001% to 10% (w/v), preferably 0.00025% to 5% (w/v), more preferably 0.0005% to 2.5% (w/v), still more preferably 0.001% to 1% (w/v), and particularly still more preferably 0.0025% to 0.5% (w/v).

The number of extracellular vesicle particles per unit volume of the storage solution according to the embodiment of the present invention is not particularly limited; however, it is for example, $2 \times 10^5$ to $2 \times 10^{16}$ (particles/mL), preferably $2 \times 10^5$ to $2 \times 10^{15}$ (particles/mL), and more preferably $2 \times 10^6$ to $2 \times 10^{14}$ (particles/mL).

The temperature in a case where the storage solution according to the embodiment of the present invention is prepared, in other words, the temperature at which the polymer according to the embodiment of the present invention is brought into contact with an extracellular vesicle is generally 2° C. to 42° C., preferably 2° C. to 40° C., and more preferably 2° C. to 37° C.

The time required for bringing the polymer according to the embodiment of the present invention into contact with an extracellular vesicle is generally 1 second to 30 minutes, preferably 1 second to 20 minutes, and more preferably 1 second to 10 minutes.

The pH of the storage solution according to the embodiment of the present invention is generally 5 to 10, preferably 5.5 to 9.5, and more preferably 5 to 9.

In the storage stabilization method according to the embodiment of the present invention, the temperature at which the storage solution according to the embodiment of the present invention is cryopreserved is not particularly limited; however, it is, for example, −2° C. to −150° C., preferably −5° C. to −150° C., and more preferably −10° C. to −150° C.

In the storage stabilization method according to the embodiment of the present invention, the storage period (the period during which the storage solution according to the embodiment of the present invention is stored at the temperature at which the storage solution according to the embodiment of the present invention is cryopreserved) of the storage solution according to the embodiment of the present invention is not particularly limited; however, it is, for example, 1 second to 5 years and preferably 5 minutes to 2 years.

The storage stabilization method according to the embodiment of the present invention may be carried out, for example, as follows.

First, an extracellular vesicle isolated from a biological specimen according to a conventional method, and a solution containing the extracellular vesicle, such as water or a buffer solution (where pH is, for example, 5 to 10, preferably 5.5 to 9.5, and more preferably 5 to 9) is obtained. Next, a separately prepared solution such as water or a buffer solution, which contains the polymer (where pH is, for example, 5 to 10, preferably 5.5 to 9.5, and more preferably 5 to 9) according to the embodiment of the present invention is added to a solution containing a biological specimen or the extracellular vesicle, and then brought to into contact (mixed) with each other, for example, at 2° C. to 42° C., preferably 2° C. to 40° C., and more preferably 2° C. to 37° C., and for example, for 1 second to 30 minutes, preferably 1 second to 20 minutes, and more preferably 1 second to 10 minutes. As a result, a storage solution (where the pH is, for example, 5 to 10, preferably 5.5 to 9.5, and more preferably 5 to 9) containing the polymer according to the embodiment of the present invention and an extracellular vesicle is obtained, where the concentration of the polymer is, for example, 0.0001% to 10% (w/v), preferably 0.00025% to 5% (w/v), more preferably 0.0005% to 2.5% (w/v), still more preferably 0.001% to 1% (w/v), and particularly preferably 0.0025% to 0.5% (w/v), and the concentration (the number of extracellular vesicle particles per unit volume of the storage solution according to the embodiment of the present invention) of the extracellular vesicle is, for example, $2 \times 10^5$ to $2 \times 10^{16}$ (particles/mL), preferably $2 \times 10^5$ to $2 \times 10^{15}$ (particles/mL), or more preferably $2 \times 10^6$ to $2 \times 10^{14}$ (particles/mL).

Next, the obtained storage solution (that is, the extracellular vesicle in the coexistence of the polymer according to the embodiment of the present invention) is cryopreserved, for example, at −2° C. to −150° C., preferably −5° C. to −150° C., and more preferably −10° C. to −150° C., and for example, for 1 second to 5 years and preferably 5 minutes to 2 years.

According to the storage stabilizer and the storage stabilization method according to the embodiment of the present invention, it is possible to stably cryopreserve the extracellular vesicle according to the embodiment of the present invention. More specifically, according to the storage stabilizer and the storage stabilization method according to the embodiment of the present invention, it is possible to significantly reduce the decrease in the number of particles of the extracellular vesicle according to the embodiment of the present invention which has been cryopreserved even in a case where the extracellular vesicle according to the embodiment of the present invention is cryopreserved as compared with a case where the stabilizer according to the embodiment of the present invention is not used. In addition, according to the storage stabilizer and the storage stabilization method according to the embodiment of the present invention, it is possible to carry out cryopreservation while maintaining the activity of the marker protein present on the membrane surface of the extracellular vesicle according to the embodiment of the present invention as compared with a case where the stabilizer according to the embodiment of the present invention is not used.

In the present invention, the thawing temperature and the thawing time in a case of thawing the cryopreserved storage solution according to the embodiment of the present invention are not particularly limited as long as they are a temperature and a time at which the extracellular vesicle can be thawed; however, the thawing temperature is, for example, 2° C. to 42° C., preferably 2° C. to 40° C., and more preferably 2° C. to 37° C., and the thawing time is, and for example, 1 second to 180 minutes, preferably 30 seconds to 120 minutes, and more preferably 1 minute to −60 minutes.

In addition, the number of times of freezing and thawing (specifically, the number of times of carrying out freezing and thawing) of the storage solution according to the embodiment of the present invention is not particularly limited; however, it is, for example, 1 to 50 times and preferably 1 to 20 times.

Specifically, the thawing method for the storage solution according to the embodiment of the present invention is carried out by thawing the storage solution according to the embodiment of the present invention which has been cryopreserved as described above, for example, at 2° C. to 42° C., preferably 2° C. to 40° C., and more preferably 2° C. to 37° C., and for example, for 1 second to 180 minutes, preferably 30 seconds to 120 minutes, and more preferably 1 minute to 60 minutes.

According to the storage stabilization method according to the embodiment of the present invention, the freezing and thawing can be repeated, for example, 1 to 50 times and preferably 1 to 20 times.

That is, the storage stabilization method according to the embodiment of the present invention can be said to be a storage stabilization method for an extracellular vesicle in freezing and thawing of the extracellular vesicle according to the embodiment of the present invention. Similarly, the storage stabilizer according to the embodiment of the present invention can be said to be a storage stabilizer for freezing and thawing of the extracellular vesicle according to the embodiment of the present invention.

INDUSTRIAL APPLICABILITY

Since the storage stabilizer and the storage stabilization method according to the embodiment of the present invention enable the stable store of the extracellular vesicle, they are useful in the fields of diagnosis and pharmaceutical products using the extracellular vesicle.

EXAMPLES

Hereinafter, the present invention will be specifically described based on Examples and Comparative Examples; however, the present invention is not limited to these Examples.

Example 1: Exosome Storage Stabilization Test Using Kollidon (Registered Trade Name) VA64

The storage stabilization effect of Kollidon (registered trade name) VA64 exosomes in the cryopreservation of the exosome was verified using an exosome derived from a COLO201 cell. Details of the measurement conditions are shown in Table 1.

(1) Acquisition of Exosome

A COLO201 cell (provided from JCRB Cell Bank) was cultured for 96 hours using Expi293 (registered trade name) Expression Medium (manufactured by Thermo Fisher Scientific, Inc.) to obtain a culture supernatant. Exosomes were purified from 10 mL of the obtained COLO201 cell culture supernatant using MagCapture (registered trade name) Exosome Isolation Kit PS (manufactured by FUJIFILM Wako Pure Chemical Corporation) according to the procedure described in the instruction manual attached to the kit to obtain the exosomes in a 1×Tris buffer (pH 7.4) containing 1 mM EDTA. The obtained solution may be abbreviated as the "purified exosome solution".

(2) Exosome Cryopreservation

The obtained purified exosome solution was incubated at 4° C. for 16 hours. Next, a 5% (w/v) Kollidon aqueous solution (Kollidon (registered trade name) VA64 (manufactured by BASF SE) and Otsuka Distilled Water (manufactured by Otsuka Pharmaceutical Co., Ltd.) were prepared. A 5% (w/v) Kollidon aqueous solution was added to the purified exosome solution after incubation to a final concentration of 0.05% (w/v). The obtained solution may be abbreviated as the "stabilizer-containing and pre-cryopreserving exosome solution".

Next, using the obtained stabilizer-containing and pre-cryopreserving exosome solution, the freezing and thawing operation was repeated 20 times under the conditions of "freezing at −80° C. for 5 minutes and then thawing at room temperature for 5 minutes". The obtained solution after freezing and thawing may be abbreviated as the "stabilizer-containing and post-cryopreserving exosome solution".

(3) Verification of Storage Stabilization Effect

CD63, which is an exosome marker, contained in the "stabilizer-containing and post-cryopreserving exosome solution" was measured according to the procedure described in the instruction manual attached to the kit by using a PS Capture (registered trade name) exosome ELISA kit (streptavidin HRP) (manufactured by FUJIFILM Wako Pure Chemical Corporation, containing an anti-CD63 antibody), and the absorbance was determined.

In addition, anti-CD9 monoclonal antibody (30B) (manufactured by FUJIFILM Wako Pure Chemical Corporation) or anti-CD81 monoclonal antibody (17B1) (011-27773, manufactured by FUJIFILM Wako Pure Chemical Corporation) was labeled by biotinylation using as a biotin labeling kit -SH (LK10, manufactured by Dojindo Molecular Technologies. Inc.). Using the obtained labeled antibody instead of the anti-CD63 antibody, CD9 and CD81, which are exosome markers, were measured by the same method, and the absorbance of each of them was obtained.

Further, as a control, CD63, CD9, and CD81 were measured by the same method using the "stabilizer-containing and pre-cryopreserving exosome solution" instead of the "stabilizer-containing and post-cryopreserving exosome solution", and the absorbance of each of them was obtained.

From the absorbance, the relative value [%] of the absorbance of each solution was calculated for each of the exosome markers, where the absorbance of the "stabilizer-containing and pre-cryopreserving exosome solution" was set to 100 [%]. The calculated value may be abbreviated as a "signal value".

(4) Result

The results of the signal value are shown in the graph of FIG. 1A. In FIG. 1A, the horizontal axis indicates the presence or absence of Kollidon (registered trade name) VA64 and the kind of the measured exosome marker, where Kollidon + indicates the result of Example 1, and Kollidon − indicates the result of Comparative Example 1 which will be described later. The vertical axis indicates the signal value.

Comparative Example 1: Exosome Storage Stabilization Test

According to the conditions described in Table 1, the measurement was carried out in the same manner as in Example 1 except that the 5% (w/v) Kollidon aqueous solution was not added to the purified exosome solution after incubation, and the signal value [%] of the exosome solution after cryopreservation was calculated.

The results of the signal value are shown in FIG. 1A. In the figure, Kollidon − indicates the result of Comparative Example 1.

From the graph of FIG. 1A, it was seen that in a case (Comparative Example 1) where only the exosome solution was cryopreserved without adding Kollidon (registered trade name) VA64, the signal value after cryopreservation was significantly decreased as compared with the signal value before cryopreservation regarding all of the exosome markers. On the other hand, in a case (Example 1) where cryopreservation was carried out with Kollidon (registered trade name) VA64 being contained, the signal values of all of the exosome markers were almost the same before and after cryopreservation, and the activity of the exosome marker was retained even after cryopreservation. That is, it has been shown that CD63, CD9, and CD81 (tetraspanin), which are exosome markers, retain a state in which they can bind to the antibody to each of them.

From these results, it has been found that the polymer having a monomer unit derived from vinylpyrrolidone has an effect of storing and stabilizing an extracellular vesicle in a case where the extracellular vesicle is cryopreserved.

Experimental Example 1: Change in Protein Concentration Before and after Exosome Storage Stabilization Test In order to confirm that the variation of the relative signal value before and after cryopreservation of an extracellular vesicle is not due to the adsorption of the extracellular vesicle to the sample tube, each of the protein concentrations of the "stabilizer-containing and pre-cryopreserving exosome solution" and the "stabilizer-containing and post-cryopreserving exosome solution" in Example 1 was measured by a BCA protein assay using PROTEIN ASSAY BCA KIT (manufactured by FUJIFILM Wako Pure Chemical Corporation). Specifically, a mixed solution was prepared by adding a 1/50 amount [v/v] of a protein assay BCA reagent B attached to the kit to a protein assay BCA reagent A attached to the kit. 200 μL of the mixed solution and 25 μL of the "stabilizer-containing and pre-cryopreserving exosome solution" or the "stabilizer-containing and post-cryopreserving exosome solution" were mixed in a NUNC 96-well plate surface plate (manufactured by Thermo Fisher Scientific, Inc.), and respective mixed solutions were incubated for 30 minutes under 60° C. conditions. Then, the absorbances of the solutions after incubation were measured at 562 nm using a plate reader, and from the measured absorbance, the protein concentrations of the "stabilizer-containing and pre-cryopreserving exosome solution" and the "stabilizer-containing and post-cryopreserving exosome solution" were respectively calculated.

The results are shown in FIG. 1B. In FIG. 1B, the horizontal axis indicates the presence or absence of Kollidon (registered trade name) VA64, where Kollidon + indicates the result of Experimental Example 1, and Kollidon − indicates the result of Experimental Example 2 which will be described later. The vertical axis indicates the measured protein concentration [ng/μL] in the solution.

Experimental Example 2: Change in Protein Concentration Before and after Exosome Storage Stabilization Test The protein concentrations of the exosome solution before cryopreservation and the exosome solution after cryopreservation in Comparative Example 1 were measured by the same method as in Experimental Example 1. Details of the measurement conditions are shown in Table 1. The results are shown in FIG. 1B. Kollidon − indicates the results of Experimental Example 2.

From FIG. 1B, it was found that there is no change in the protein concentration of the exosome solution before and after cryopreservation regardless of whether Kollidon (registered trade name) VA64 is used or not. From the results of FIG. 1A and FIG. 1B, it was confirmed that the variation of the signal value before and after cryopreservation of the extracellular vesicle is not due to the adsorption of the extracellular vesicle to the sample tube.

Experimental Example 3: Change in Number of Particles Before and after Exosome Storage Stabilization Test The numbers of particles per unit volume of the "stabilizer-containing and pre-cryopreserving exosome solution" and the "stabilizer-containing and post-cryopreserving exosome solution" in Example 1 were respectively measured three times according to the procedure described in the NanoSight instruction manual by a nanoparticle tracking analysis method (a Nano Tracking Analysis method) using NanoSight (manufactured by Malvern Panalytical Ltd.), and the average number of particles [particles/mL] per unit volume was calculated.

Figure 1C:
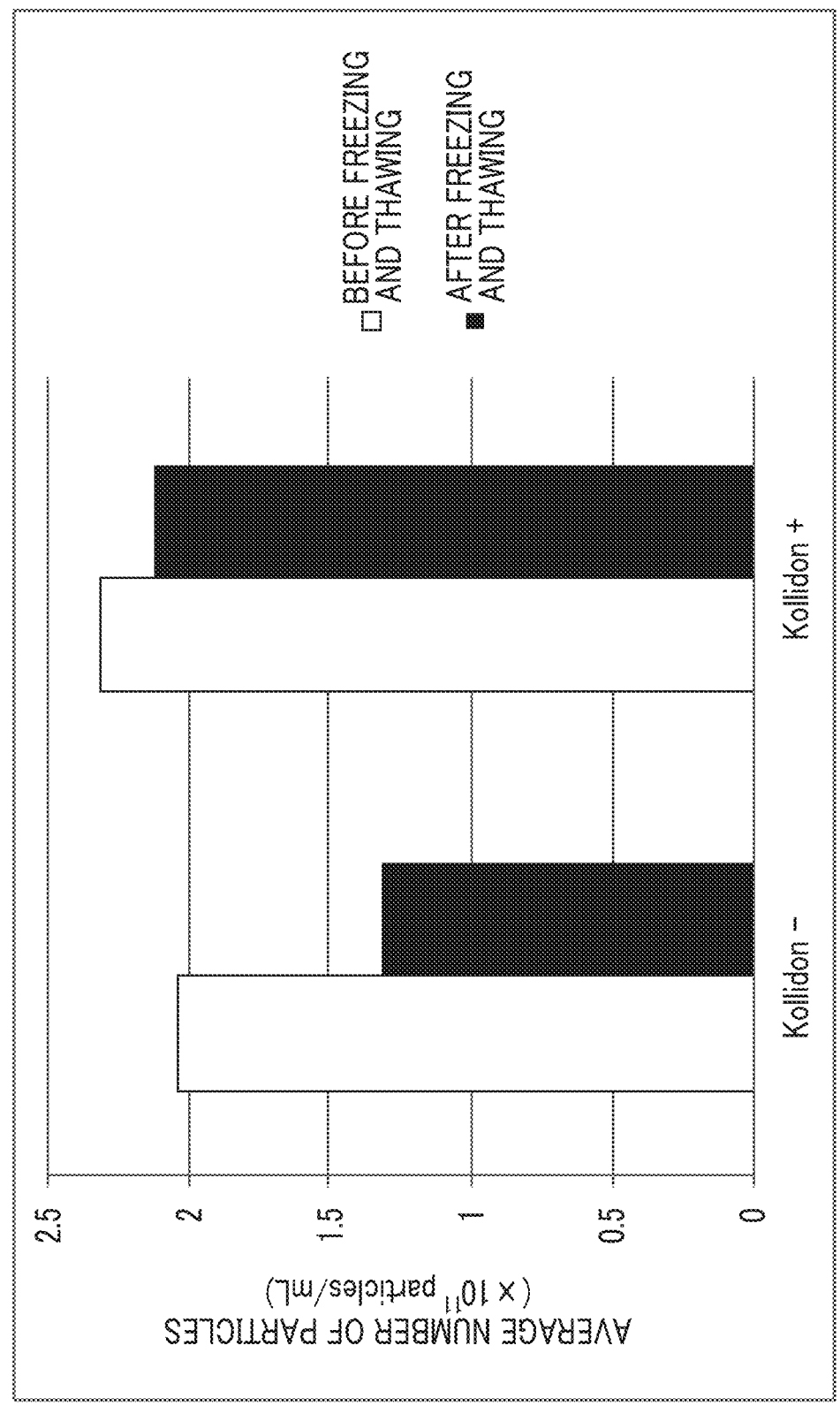
FIG. 1C is a graph showing results of verifying changes in the number of particles before and after an exosome storage stabilization test, which are obtained from Experimental Example 3 and Experimental Example 4.

The results are shown in FIG. 1C. In FIG. 1C, the horizontal axis indicates the presence or absence of Kollidon (registered trade name) VA64, where Kollidon + indicates the result of Experimental Example 3, and Kollidon − indicates the result of Experimental Example 4 which will be described later. The vertical axis indicates the number of particles in the measured solution [×$10^{11}$ particles/mL].

Experimental Example 4: Change in Number of Particles Before and after Exosome Storage Stabilization Test The numbers of particles per unit volume of the exosome solution before cryopreservation and the exosome solution after cryopreservation in Comparative Example 1 were measured by the same method as in Experimental Example 3, and the average number of particles per unit volume [particles/mL] was calculated.

The results are shown in FIG. 1C. Kollidon − indicates the results of Experimental Example 4.

From FIG. 1C, it was seen that in a case (Experimental Example 4) where only the exosome solution was cryopreserved without adding Kollidon (registered trade name) VA64, the number of particles was significantly reduced after the cryopreservation. On the other hand, in a case (Experimental Example 3) where cryopreservation was carried out with Kollidon (registered trade name) VA64 being contained, the number of particles was almost the same before and after cryopreservation.

Figure 1D:
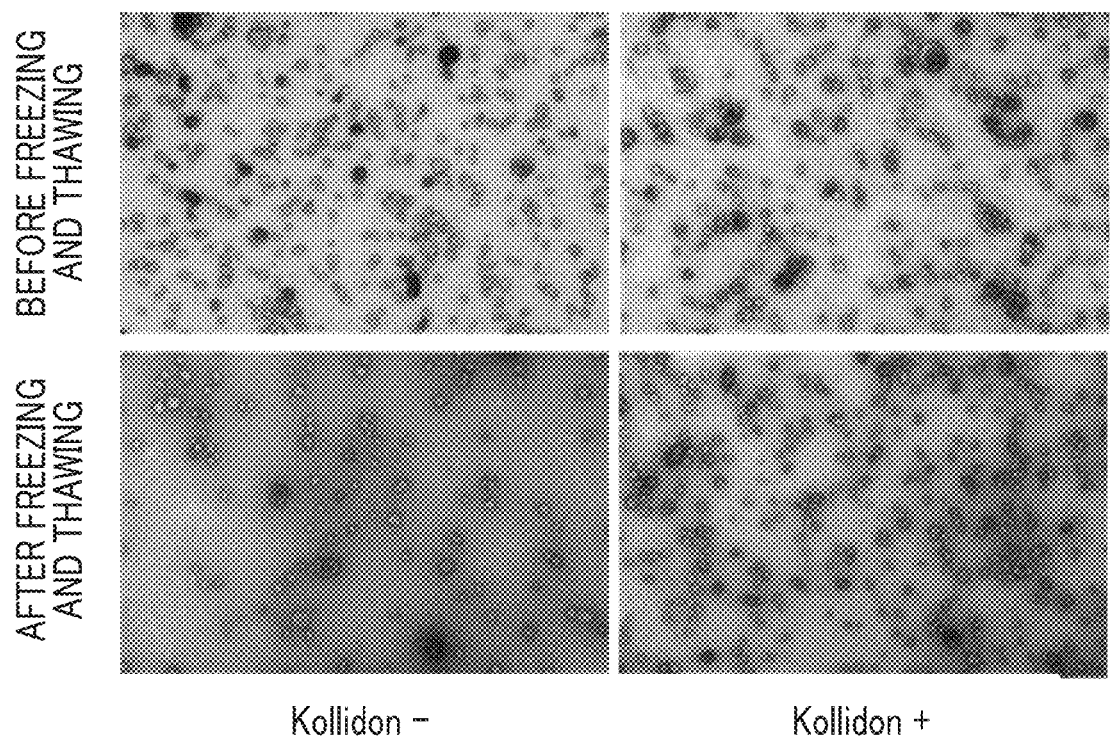
FIG. 1D shows electron microscopic observation images in which changes in the number of particles before and after an exosome storage stabilization test were verified, which are obtained from Example 2 and Comparative Example 2.

Example 2: Change in Number of Particles Before and after Exosome Storage Stabilization Test In order to verify that the number of particles is reduced by the cryopreservation of the extracellular vesicle, the "stabilizer-containing and pre-cryopreserving exosome solution" and the "stabilizer-containing and post-cryopreserving exosome solution" in Example 1 were analyzed using a transmission electron microscope (TEM). The images observed by the transmission electron microscope are shown in FIG. 1D. In FIG. 1D, Kollidon + indicates the result of Example 2, and Kollidon − indicates the result of Comparative Example 2 which will be described later.

Comparative Example 2: Change in Number of Particles Before and after Exosome Storage Stabilization Test The exosome solution before cryopreservation and the exosome solution after cryopreservation in Comparative Example 1 were analyzed using a transmission electron microscope (TEM) by the same method as in Example 2. The images observed by the transmission electron microscope are shown in FIG. 1D.

From FIG. 1D, it was observed that in a case (Comparative Example 2) where only the exosome solution was cryopreserved without adding Kollidon (registered trade name) VA64, the particles were decreased after the cryopreservation. On the other hand, in a case (Example 2) where cryopreservation was carried out with Kollidon (registered trade name) VA64 being contained, no significant change was observed before and after cryopreservation.

From FIG. 1C and FIG. 1D, it was found that the polymer having a monomer unit derived from vinylpyrrolidone has an effect of storing and stabilizing an extracellular vesicle while substantially maintaining the number of particles in a case of cryopreserving the extracellular vesicle.

In addition, from FIG. 1B to FIG. 1D, it was found that the reason for the variation of the signal value before and after cryopreservation of the extracellular vesicle is not due to the adsorption of the extracellular vesicle to the sample tube but due to the decrease in the number of extracellular vesicle particles.

Example 3: Storage Stabilization Test Using Exosomes Derived from Various Specimens It was examined whether the storage stabilization effect of Kollidon (registered trade name) VA64 in the exosome cryopreservation is also effective on exosomes derived from various specimens. That is, the examination was carried out using, as specimens, each of 1 mL of a COLO201 cell culture supernatant obtained by the same method as in Example 1, 1 mL of a mesenchymal stem cell (MSC) (manufactured by Lonza) culture supernatant obtained by the same method as in Example 1, 1 mL of serum (manufactured by BizCom Japan, Inc.), and 1 mL of plasma (manufactured by BizCom Japan, Inc.).

Specifically, the absorbance was measured according to the method described in Example 1 based on the conditions shown in Table 1, and the signal value was calculated. It should be noted that as a result of measuring the number of particles per unit volume of the specimen by the same method as in Experimental Example 3, the number of particles per unit volume of the COLO201 cell culture supernatant was $2 \times 10^{10}$ particles/mL, the number of particles per unit volume of the mesenchymal stem cell culture supernatant was $2 \times 10^9$ particles/mL, the number of particles per unit volume of serum was $2 \times 10^{10}$ particles/mL, and the number of particles per unit volume of plasma was $6 \times 10^{10}$ particles/mL.

Figure 2:
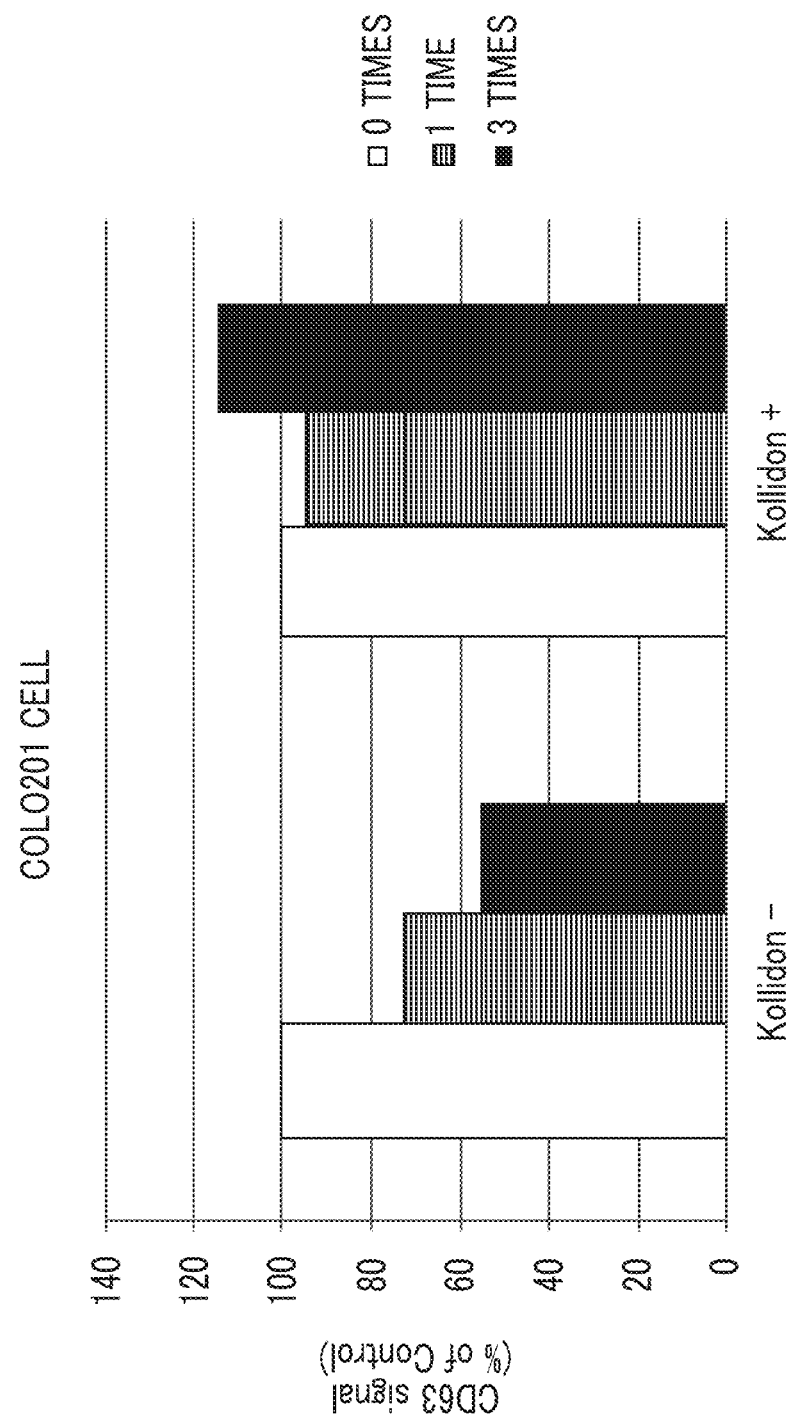
FIG. 2 is a graph showing results of storage stabilization tests using exosomes derived from the culture supernatant of COLO201 cells, which are obtained from Example 3 and Comparative Example 3.
Figure 3:
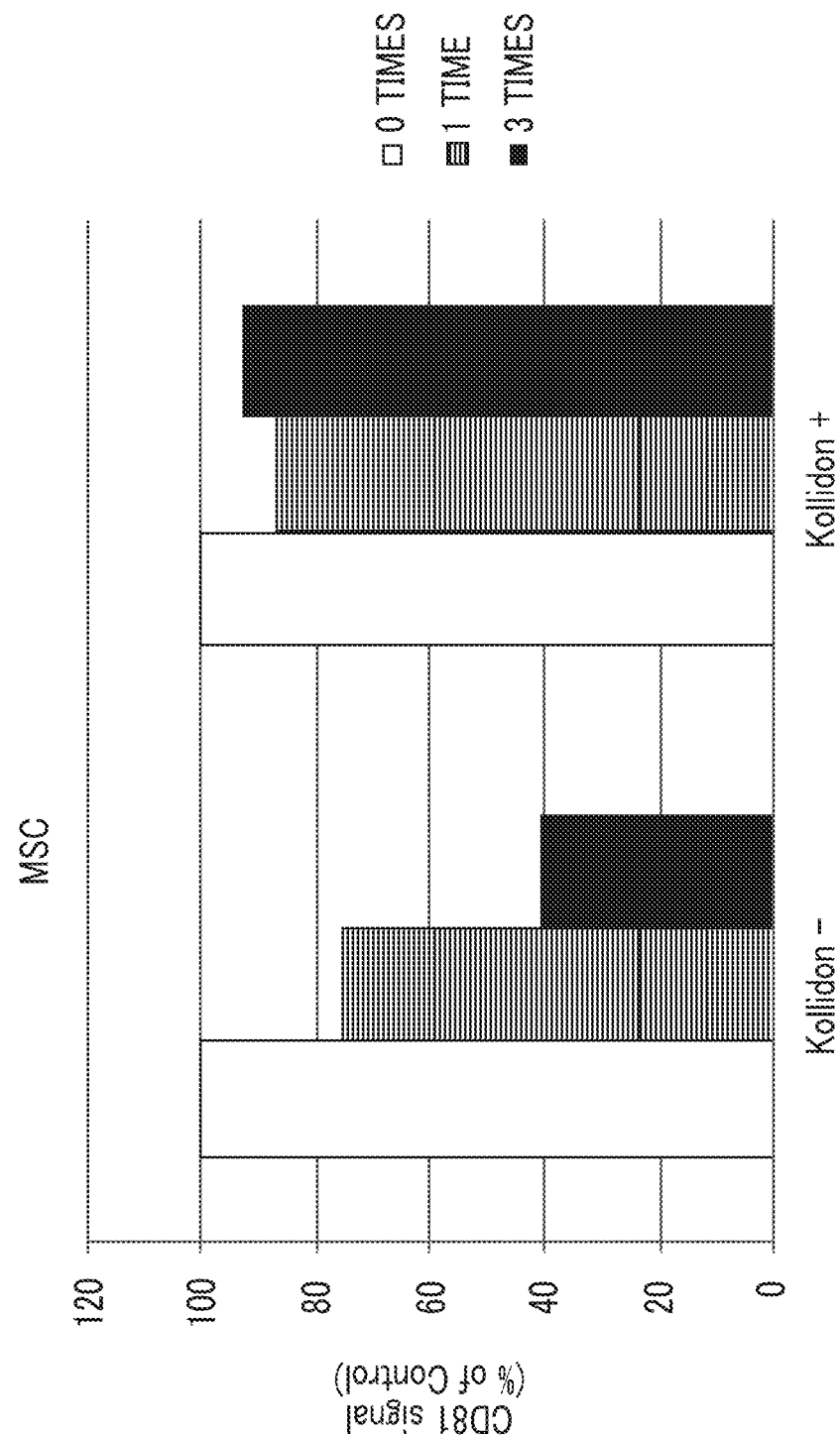
FIG. 3 is a graph showing results of storage stabilization tests using exosomes derived from the culture supernatant of mesenchymal stem cells (MSCs), which are obtained from Example 3 and Comparative Example 3.
Figure 4:
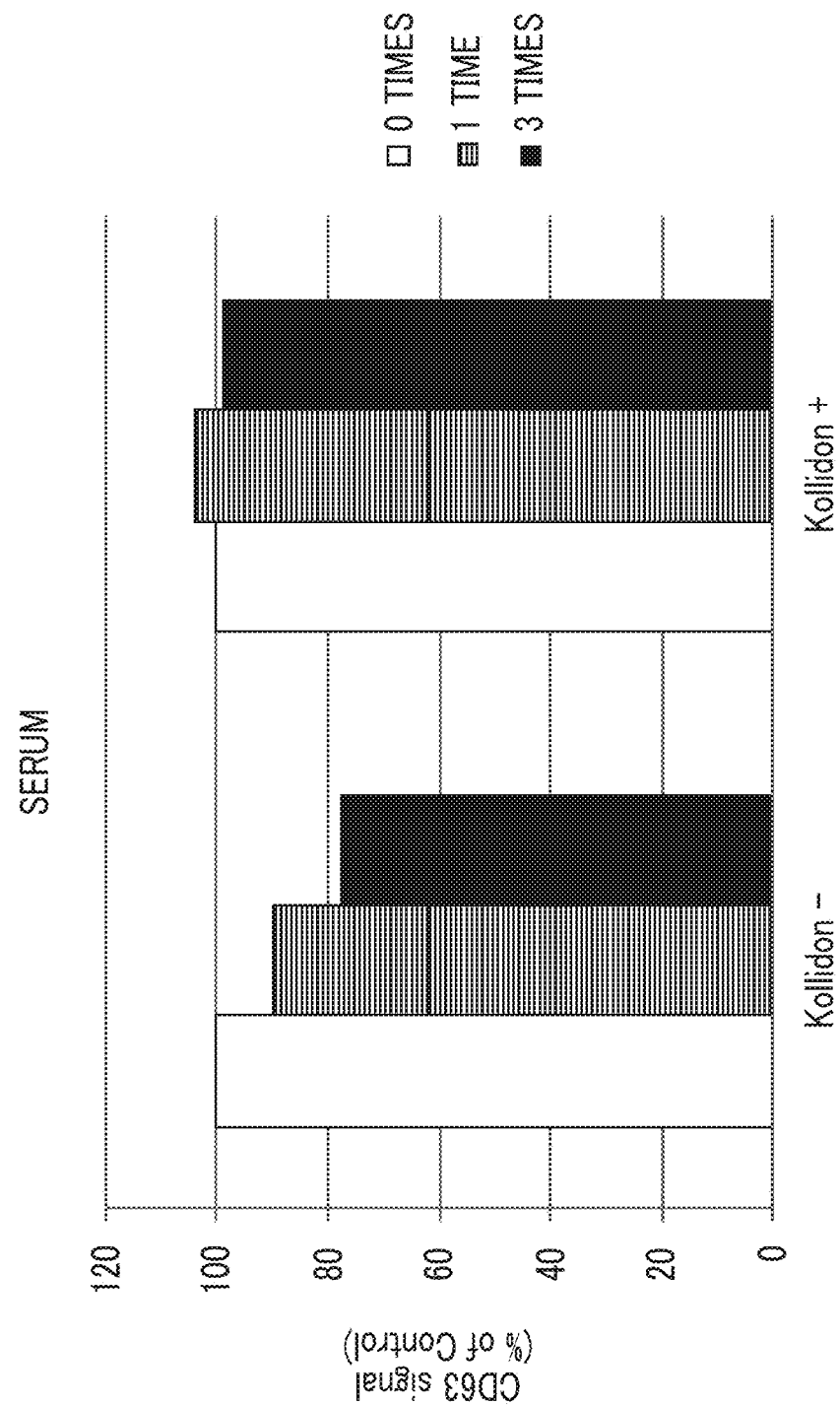
FIG. 4 is a graph showing results of storage stabilization tests using exosomes derived from serum, which are obtained from Example 3 and Comparative Example 3.
Figure 5:
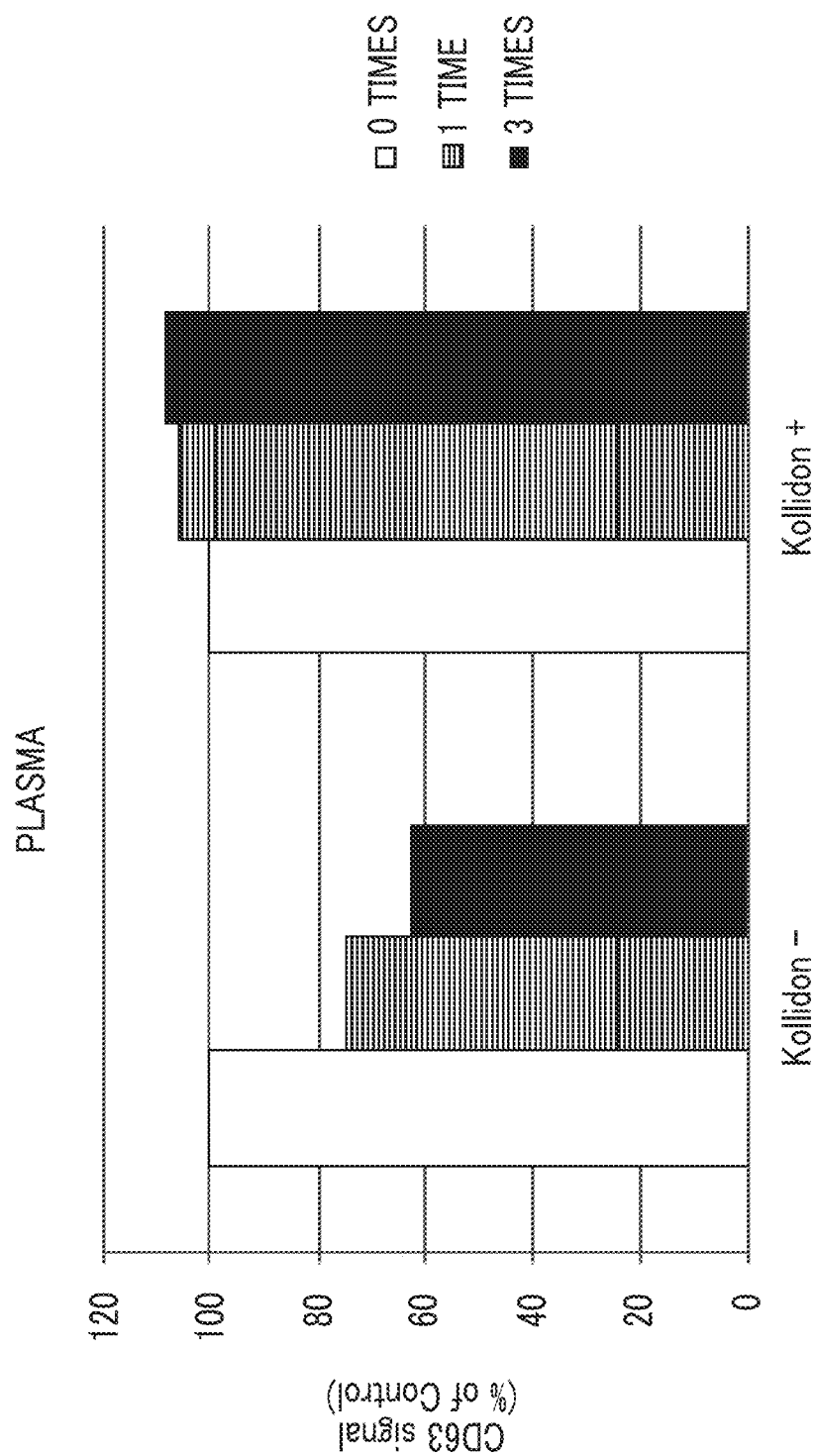
FIG. 5 is a graph showing results of storage stabilization tests using exosomes derived from plasma, which are obtained from Example 3 and Comparative Example 3.

The results of the signal values are shown in FIG. 2 to FIG. 5, respectively. FIG. 2 shows the results in a case where the exosome derived from the COLO201 cell is used, FIG. 3 shows the results in a case where the exosome derived from the mesenchymal stem cell (MSC) is used, FIG. 4 shows the results in a case where the exosome derived from serum is used, and FIG. 5 shows the results in a case where the exosome derived from plasma is used. In the figure, the horizontal axis indicates the presence or absence of Kollidon (registered trade name) VA64 and the number of times of freezing and thawing operation, where Kollidon + indicates the result of Example 3, and Kollidon − indicates the result of Comparative Example 3 which will be described later.

The vertical axis indicates the signal value [%].

Comparative Example 3: Storage Stabilization Test Using Exosome Derived from Different Specimen According to the conditions described in Table 1, the measurement was carried out in the same manner as in Example 3 except that the operation of adding the 5% (w/v) Kollidon aqueous solution to the purified exosome solution after incubation was not carried out, and the signal value [%] of the exosome solution after cryopreservation was calculated.

The results of the signal values are shown in FIG. 2 to FIG. 5, respectively. In the figure, Kollidon − indicates the result of Comparative Example 3.

From the graphs of FIG. 2 to FIG. 5, it was seen that in a case where Kollidon (registered trade name) VA64 was used, the signal values were almost the same before and after cryopreservation in all of the case (FIG. 3) where the exosome derived from the mesenchymal stem cell (MSC) was used, the case (FIG. 4) where the exosome derived from serum was used, and the case (FIG. 5) where the exosome derived from plasma was used, similarly as in the case (FIG. 2) where the exosome derived from the COLO201 cell was used.

From these results, it has been found that the polymer having a monomer unit derived from vinylpyrrolidone has an effect of stabilizing an extracellular vesicle regardless of the origin of the extracellular vesicle in a case where the extracellular vesicle is cryopreserved.

Example 4: Effect of Freezing Temperature on Storage Stabilization of Exosome

The effect of the exosome freezing temperature on the storage stabilization effect of Kollidon (registered trade name) VA64 in the exosome cryopreservation was verified. That is, the examination was carried out with the freezing temperature being set to −80° C. or −20° C.

Figure 6:
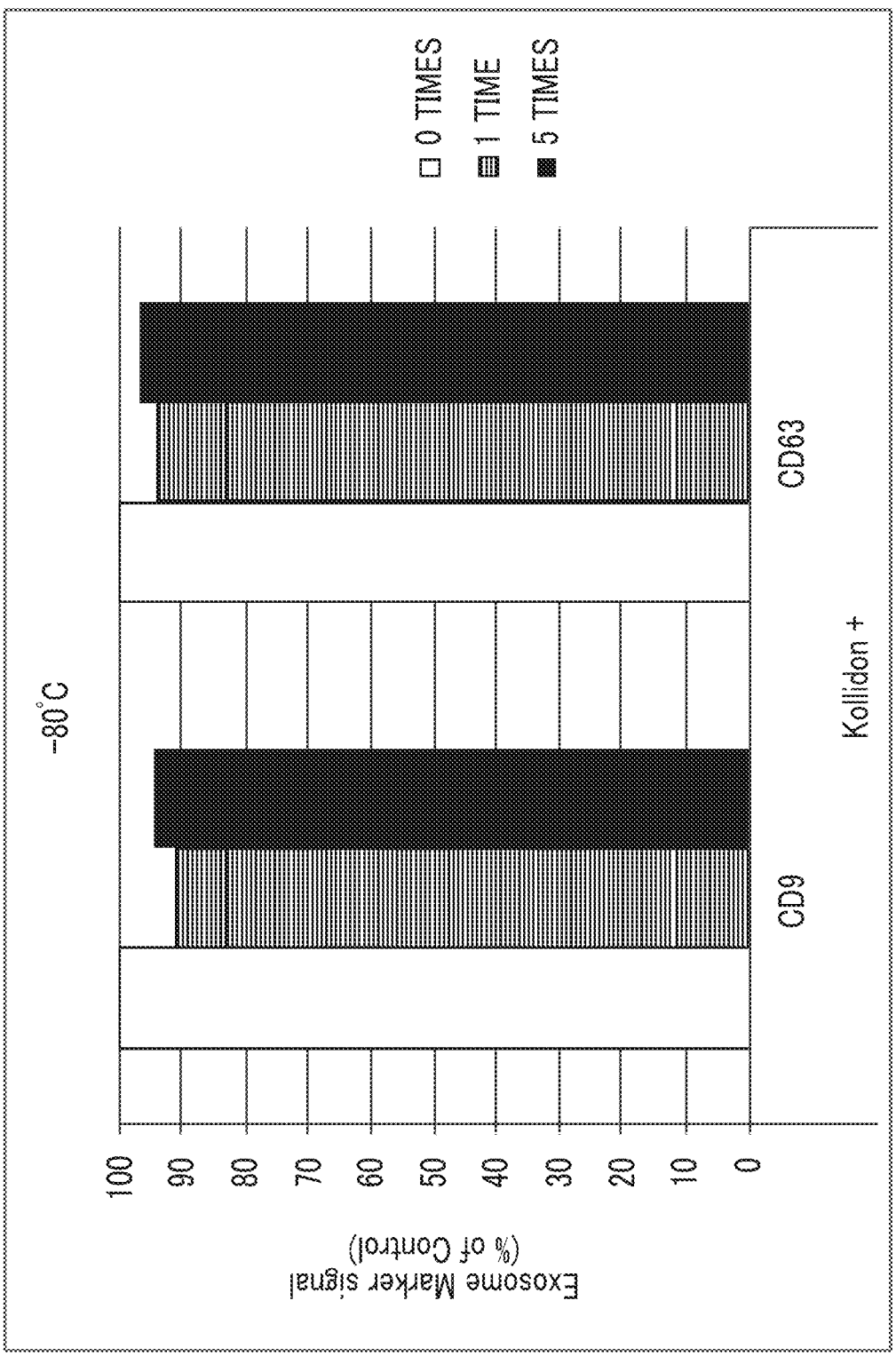
FIG. 6 is a graph showing results of verifying effects of the freezing temperature (−80° C.) on the storage stabilization of exosomes with a stabilization test, which are obtained from Example 4.
Figure 7:
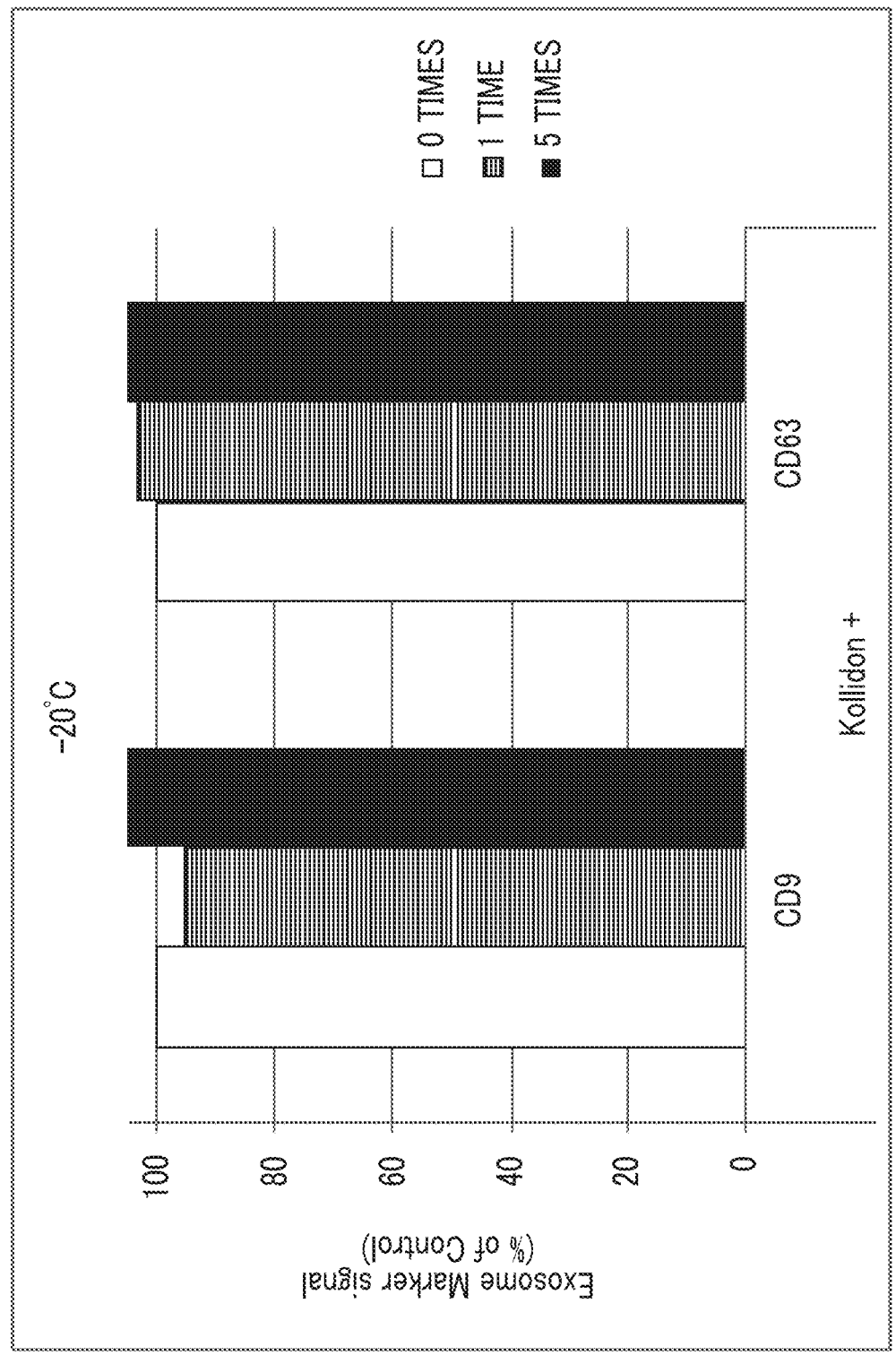
FIG. 7 is a graph showing results of verifying effects of the freezing temperature (−20° C.) on the storage stabilization of exosomes with a stabilization test, which are obtained from Example 4.

Specifically, the absorbance was measured according to the method described in Example 1 based on the conditions shown in Table 1, and the signal value was calculated. The results of the signal values are shown in the graphs of FIG. 6 and FIG. 7, respectively. FIG. 6 shows the result in a case where the cryopreservation was carried out at −80° C., and FIG. 7 shows the result in a case where the cryopreservation was carried out at −20° C. In the figure, Kollidon + indicates the result of Example 4, and Kollidon − indicates the result of Comparative Example 4 which will be described later. The horizontal axis indicates the number of times of freezing and thawing operation and the kind of the detected exosome marker. The vertical axis indicates the signal value [%].

From the graphs of FIG. 6 and FIG. 7, it was seen that the signal values of CD9 and CD63, which are exosome markers, were almost the same before and after cryopreservation at both the freezing temperatures of −20° C. and −80° C.

From these results, it has been found that the polymer having a monomer unit derived from vinylpyrrolidone has an effect of stabilizing an extracellular vesicle regardless of the freezing temperature of the extracellular vesicle in a case where the extracellular vesicle is cryopreserved.

Example 5: Effect of Number of Times of Freezing and Thawing Operation on Storage Stabilization of Exosome The effect of the number of times of freezing and thawing operation on the storage stabilization effect of Kollidon (registered trade name) VA64 in the exosome cryopreservation was verified in a case where the freezing temperature was −20° C. That is, the examination was carried out by setting the freezing temperature to −20° C. and the number of times freezing and thawing operation to 15 times. Specifically, the absorbance was measured according to the method described in Example 1 based on the conditions shown in Table 1, and the signal value was calculated.

Figure 8:
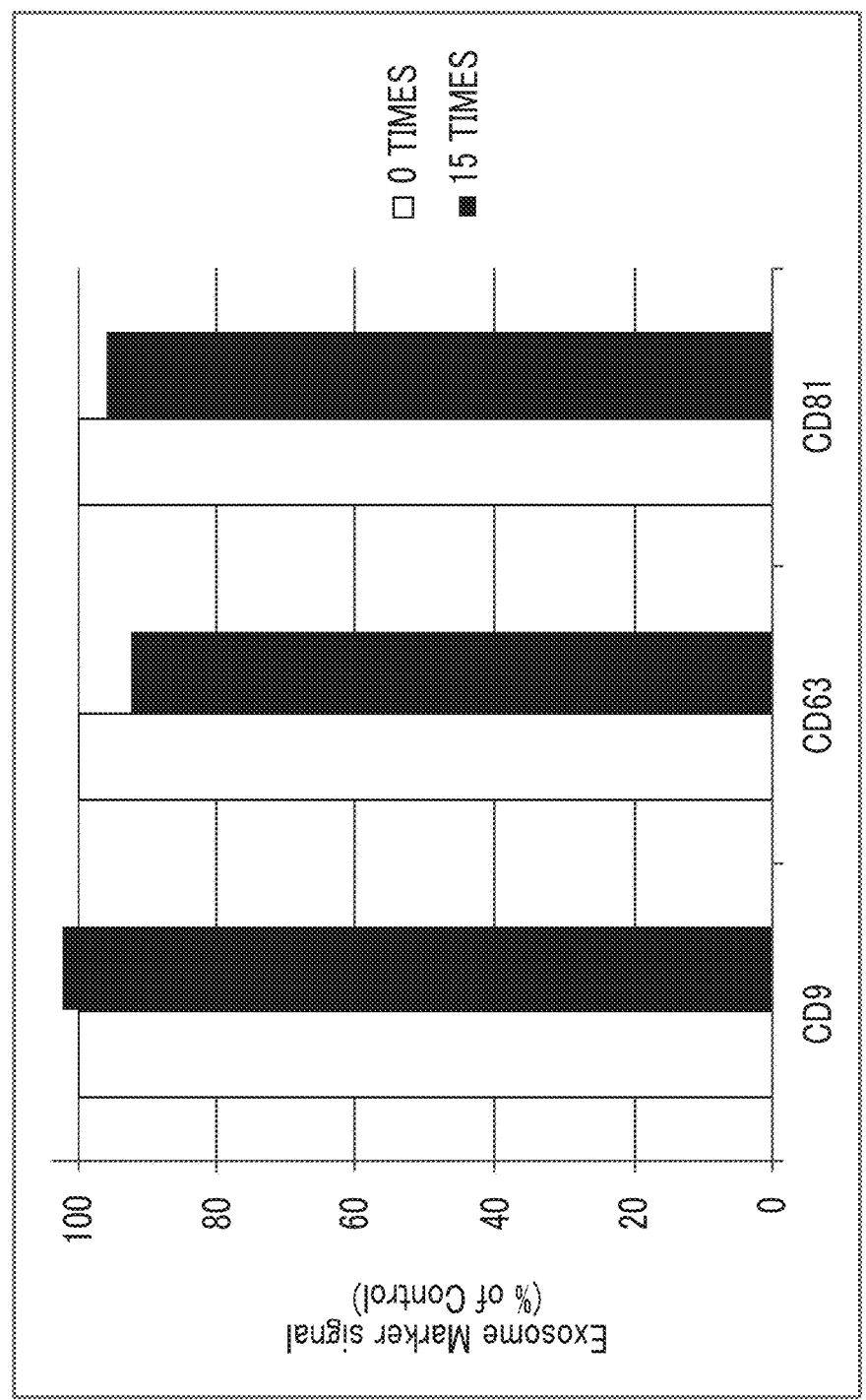
FIG. 8 is a graph showing results of verifying effects of the number of times of freezing and thawing operation on the storage stabilization of exosomes with a stabilization test, which are obtained from Example 5.

The results of the signal values are shown in FIG. 8. In the graph, the horizontal axis indicates the number of times of freezing and thawing operation and the kind of the detected exosome marker. The vertical axis indicates the signal value [%].

Example 6: Effect of Number of Times of Freezing and Thawing Operation on Storage Stabilization of Exosome The effect of the number of times of freezing and thawing operation on the storage stabilization effect of Kollidon (registered trade name) VA64 in the exosome cryopreservation was verified. That is, the exosomes after carrying out the freezing and thawing operation 15 times in Example 5 were analyzed using a transmission electron microscope (TEM). In addition, as a control, exosomes before the freezing and thawing operation were also observed by the same method. The images observed by the transmission electron microscope are shown in FIG. 9. In the figure, the upper part is an observation image before the freezing and thawing operation (0 times), and the lower part is an observation image after the freezing and thawing operation was carried out 15 times.

From the graph of FIG. 8, it could be seen that even in a case where the freezing temperature was set to −20° C. and the freezing and thawing operation was carried out 15 times, the signal values of all of the exosome markers were almost the same before and after the cryopreservation.

In addition, from the images observed by the electron microscope in FIG. 9, it was seen that in a case where the extracellular vesicles were subjected to the freezing and thawing operation 15 times at −20° C. using Kollidon (registered trade name) VA64, the shape change before and after cryopreservation was not observed, and the number of particles was substantially maintained.

From the results, it has been found that the polymer having a monomer unit derived from vinylpyrrolidone has an effect of stabilizing an extracellular vesicle regardless of the number of times of cryopreservation operation of the extracellular vesicle in a case where the extracellular vesicle is cryopreserved.

Comparative Example 4: Exosome Storage Stabilization Test Using Trehalose

It has been suggested that trehalose protects and stabilizes exosomes from damage caused by cryopreservation, by suppressing the aggregation of exosomes and maintaining the number of particles in the exosome cryopreservation (Non-Patent Literature 1). For this reason, it was verified whether trehalose could not only suppress the decrease in the number of particles during cryopreservation but also retain the activity of the exosome marker (the exosome surface antigen), similarly to the stabilizer according to the embodiment of the present invention.
(1) Acquisition of Exosome
Exosomes were purified from the culture supernatant of the COLO201 cell by the same method as in Example 1 to obtain a purified exosome solution.
(2) Exosome Cryopreservation
The obtained purified exosome solution was incubated at 4° C. for 16 hours. Next, trehalose (manufactured by FUJIFILM Wako Pure Chemical Corporation) was dissolved in Otsuka Distilled Water (manufactured by Otsuka Pharmaceutical Co., Ltd.) to prepare a 500 mM trehalose aqueous solution. The 500 mM trehalose aqueous solution was added to the purified exosome solution after incubation to a final concentration of 25 mM. The obtained solution may be abbreviated as the "trehalose-containing and pre-cryopreserving exosome solution". Next, using the exosome solution to which trehalose had been added, the freezing and thawing operation was repeated 3 times under the conditions of freezing at −80° C. for 5 minutes and then thawing at room temperature for 5 minutes. The obtained solution may be abbreviated as the "trehalose-containing and post-cryopreserving exosome solution".
(3) Absorbance Measurement of Exosome Marker
CD9, which is an exosome marker, in the "trehalose-containing and pre-cryopreserving exosome solution" was measured according to the procedure described in the instruction manual attached to the kit by using a PS Capture (registered trade name) exosome ELISA kit (streptavidin HRP) (manufactured by FUJIFILM Wako Pure Chemical Corporation), and the absorbance was calculated. However, in order to detect CD9, an anti-CD9 and a monoclonal antibody (30B) (FUJIFILM Wako Pure Chemical Corporation), which had been labeled by biotinylation using a biotin labeling kit-SH (LK10, manufactured by Dojindo Molecular Technologies. Inc.) were used instead of the anti-CD63 antibody in the kit.

Further, as a control, CD9 was measured by the same method using the "trehalose-containing and pre-cryopreserving exosome solution" instead of the "trehalose-containing and post-cryopreserving exosome solution", and the absorbance of each of them was obtained.

Figure 10:
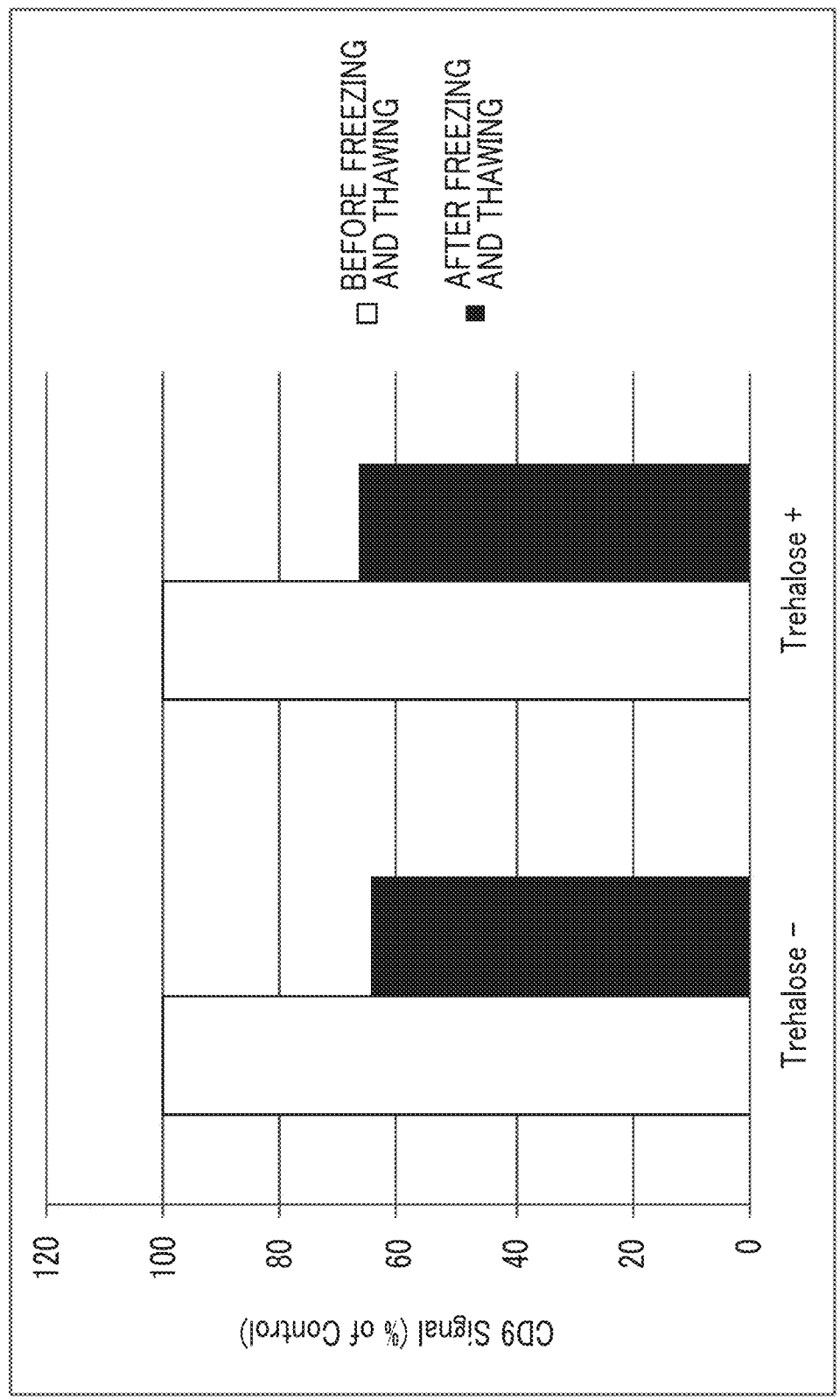
FIG. 10 is a graph showing results of exosome storage stabilization tests using trehalose, which are obtained from Comparative Example 4 and Comparative Example 5.

From the absorbance, the relative value [%] of the absorbance of each solution was calculated for each of the exosome markers, where the absorbance of the "trehalose-containing and pre-cryopreserving exosome solution" was set to 100 [%]. The calculated value may be abbreviated as a "signal value".
(4) Result
The results of the signal value are shown in the graph of FIG. 10. In the figure, trehalose + indicates the result of Comparative Example 4, and trehalose − indicates the result of Comparative Example 5 which will be described later. In FIG. 10, the horizontal axis indicates the presence or absence of trehalose. In addition, the vertical axis indicates the signal value.

Comparative Example 5: Exosome Storage Stabilization Test

According to the conditions shown in Table 1, the measurement was carried out in the same manner as in Comparative Example 4 except that the 500 mM trehalose aqueous solution was not added to the purified exosome solution after incubation, and the signal value [%] was calculated.

The results of the signal value are shown in FIG. 10. In the graph, trehalose − indicates the result of Comparative Example 5.

From the graph of FIG. 10, it was seen that in a case (Comparative Example 5) where only the exosome solution was cryopreserved without adding trehalose, the signal value after cryopreservation was significantly decreased as compared with the signal value before cryopreservation regarding all the exosome markers. On the other hand, also in the case (Comparative Example 4) where cryopreservation was carried out with trehalose being contained, the signal value of the exosome marker was significantly reduced.

From the results of Comparative Example 4 and Comparative Example 5, it was found that the activity of the exosome marker (the exosome surface antigen) cannot be retained even in a case where trehalose is used, although it has been suggested that trehalose suppresses the decrease in the number of particles during exosome cryopreservation.

Example 6: Exosome Storage Stabilization Test Using Kollidon (Registered Trade Name) 17PF The storage stabilization effect of polyvinylpyrrolidone in the cryopreservation was examined using Kollidon (registered trade name) 17PF and the exosome derived from the culture supernatant of the COLO201 cell.
(1) Acquisition of Exosome
Exosomes were purified from the culture supernatant of the COLO201 cell by the same method as in Example 1 to obtain a purified exosome solution.
(2) Cryopreservation and Thawing of Exosome
The obtained purified exosome solution was incubated at 4° C. for 16 hours. Next, Kollidon (registered trade name) 17PF (manufactured by BASF SE), which is a commercially available polyvinylpyrrolidone, was dissolved in Otsuka Distilled Water to prepare a 10% (w/v) Kollidon (registered trade name) 17PF aqueous solution. The 10% Kollidon (registered trade name) 17PF aqueous solution was added to the purified exosome solution after incubation to a final concentration of 0.1%. The obtained solution may be abbreviated as the "Kollidon (registered trade name) 17PF-containing, pre-freezing-thawing, and pre-cryopreserving exosome solution". Next, the exosome solution to which Kollidon (registered trade name) 17PF had been added was subjected to the freezing and thawing operation three times under the conditions in which the exosome solution is allowed to freeze at −80° C. for 5 minutes and then allowed to thaw at room temperature for 5 minutes. The obtained solution may be abbreviated as the "Kollidon (registered trade name) 17PF-containing, post-freezing-thawing, and post-cryopreserving exosome solution".

(3) Verification of Storage Stabilization Effect

CD9, which is an exosome marker, was measured to obtain the absorbance, according to the procedure described in the instruction manual attached to the kit, except that the "Kollidon (registered trade name) 17PF-containing, post-freezing-thawing, and post-cryopreserving exosome solution" was used as a measurement specimen and an anti-CD9 antibody was used instead of the anti-CD63 antibody in a PS Capture (registered trade name) exosome ELISA kit (streptavidin HRP) (FUJIFILM Wako Pure Chemical Corporation, containing an anti-CD63 antibody). As the anti-CD9 antibody, an anti-CD9 and a monoclonal antibody (30B) (FUJIFILM Wako Pure Chemical Corporation), which had been labeled by biotinylation using a biotin labeling kit-SH (LK10, manufactured by Dojindo Molecular Technologies. Inc.) were used. Further, as a control, the "Kollidon (registered trade name) 17PF-containing, pre-freezing-thawing, and pre-cryopreserving exosome solution" was used, and CD9 was measured by the same method to obtain absorbance.

From the obtained absorbance, the relative value [%] (signal value) of the absorbance of each solution of the "Kollidon (registered trade name) 17PF-containing, post-freezing-thawing, and post-cryopreserving exosome solution" was calculated, where the absorbance of the "Kollidon (registered trade name) 17PF-containing, pre-freezing-thawing, and pre-cryopreserving exosome solution" was set to 100 [%].

(4) Result

Figure 11:
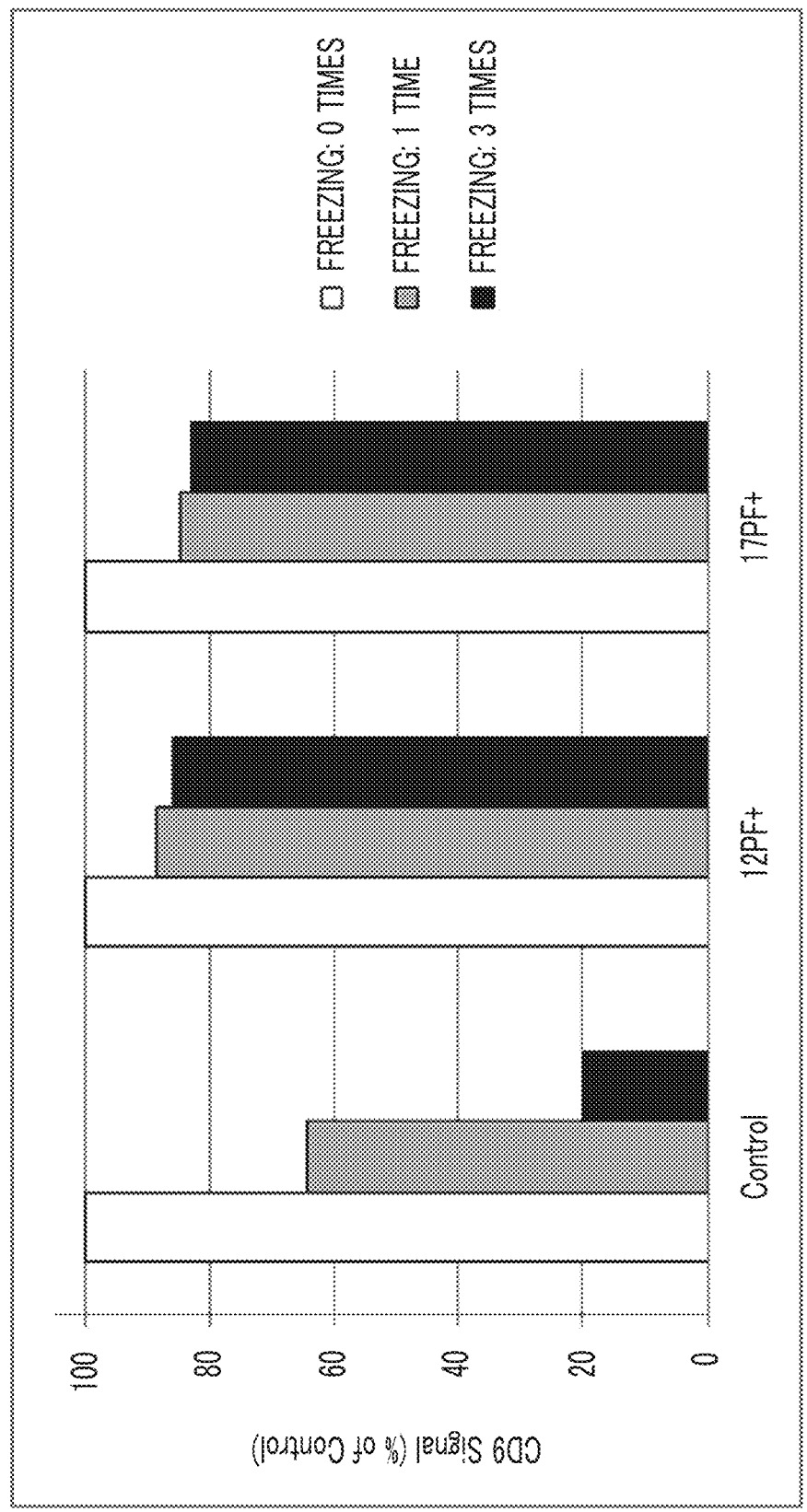
FIG. 11 is a graph showing results of storage stabilization tests using Kollidon (registered trade name) 12PF or 17PF, which are obtained from Examples 7 to 8 and Comparative Example 6.

The results of the signal value are shown in the graph of FIG. 11. In FIG. 11, the horizontal axis indicates the kind and the presence or absence of Kollidon (registered trade name), and the vertical axis indicates the signal value. In the graph, 17PF+indicates the result of Example 6.

Example 7: Exosome Storage Stabilization Test Using Kollidon (Registered Trade Name) 12PF CD9 was measured by the same method as in Example 6 except that "Kollidon (registered trade name) 12PF" was used instead of "Kollidon (registered trade name) 17PF", and the relative signal value was calculated. The results of the relative signal value are shown in the graph of FIG. 11. In the graph, 12PF+indicates the result of Example 7.

Comparative Example 6: Effect of Freezing and Thawing on Stabilization of Exosome According to the conditions described in Table 1, the measurement was carried out in the same manner as in Example 6 except that the 10% (w/v) Kollidon 12PF aqueous solution was not added to the purified exosome solution after incubation, and the signal value [%] was calculated. The results of the signal value are shown in the graph of FIG. 11. In the graph, Control indicates the result of Comparative Example 6.

From the graph of FIG. 11, it was seen that in a case (Comparative Example 6) where only the exosome solution was cryopreserved without using Kollidon (registered trade name) 17PF or Kollidon (registered trade name) 12PF, the signal value after cryopreservation was significantly decreased as compared with the signal value before cryopreservation.

On the other hand, in a case where cryopreservation was carried out using each of Kollidon (registered trade name) 17PF and Kollidon (registered trade name) 12PF (Examples 6 and 7), the signal value was individually almost the same before and after cryopreservation regardless of the number of times of cryopreservation, similarly as in the case where the cryopreservation was carried out using Kollidon (registered trade name) VA64.

From these results, it has been found that polyvinylpyrrolidone also has an effect of storing and stabilizing an extracellular vesicle in a case where the extracellular vesicle is cryopreserved.

The experimental conditions of Example 1 to 8, Comparative Example 1 to 6, and Experimental Examples 1 to 4, and the numbers of the figures showing the results are summarized in Table 1 below.

TABLE 1

| Number of Example/ Comparative Example | Figure | Specimen | Polymer or Trehalose | Number of times of freezing and thawing operation | Freezing temperature | Antibody used for detection | Experimental method |
|---|---|---|---|---|---|---|---|
| Example 1 | FIG. 1A | COLO201 cell culture supernatant | VA64 | 20 | −80° C. | CD9 antibody | ELISA method |
| Example 1 | FIG. 1A | COLO201 cell culture supernatant | VA64 | 20 | −80° C. | CD63 antibody | ELISA method |
| Example 1 | FIG. 1A | COLO201 cell culture supernatant | VA64 | 20 | −80° C. | CD81 antibody | ELISA method |
| Comparative Example 1 | FIG. 1A | COLO201 cell culture supernatant | — | 20 | −80° C. | CD9 antibody | ELISA method |
| Comparative Example 1 | FIG. 1A | COLO201 cell culture supernatant | — | 20 | −80° C. | CD63 antibody | ELISA method |

TABLE 1-continued

| Number of Example/ Comparative Example | Figure | Specimen | Polymer or Trehalose | Number of times of freezing and thawing operation | Freezing temperature | Antibody used for detection | Experimental method |
|---|---|---|---|---|---|---|---|
| Comparative Example 1 | FIG. 1A | COLO201 cell culture supernatant | — | 20 | −80° C. | CD81 antibody | ELISA method |
| Experimental Example 1 | FIG. 1B | COLO201 cell culture supernatant | VA64 | 20 | −80° C. | — | BCA protein assay |
| Experimental Example 2 | FIG. 1B | COLO201 cell culture supernatant | — | 20 | −80° C. | — | BCA protein assay |
| Experimental Example 3 | FIG. 1C | COLO201 cell culture supernatant | VA64 | 20 | −80° C. | — | Nanoparticle tracking analysis method |
| Experimental Example 4 | FIG. 1C | COLO201 cell culture supernatant | — | 20 | −80° C. | — | Electron microscopic observation |
| Example 2 | FIG. 1D | COLO201 cell culture supernatant | VA64 | 20 | −80° C. | — | Electron microscopic observation |
| Comparative Example 2 | FIG. 1D | COLO201 cell culture supernatant | — | 20 | −80° C. | CD63 antibody | ELISA method |
| Example 3 | FIG. 2 | COLO201 cell culture supernatant | VA64 | 1 | −80° C. | CD63 antibody | ELISA method |
| Example 3 | FIG. 2 | COLO201 cell culture supernatant | VA64 | 3 | −80° C. | CD81 antibody | ELISA method |
| Example 3 | FIG. 3 | Mesenchymal stem cell culture supernatant | VA64 | 1 | −80° C. | CD81 antibody | ELISA method |
| Example 3 | FIG. 3 | Mesenchymal stem cell culture supernatant | VA64 | 3 | −80° C. | CD63 antibody | ELISA method |
| Example 3 | FIG. 4 | Serum | VA64 | 1 | −80° C. | CD63 antibody | ELISA method |
| Example 3 | FIG. 4 | Serum | VA64 | 3 | −80° C. | CD63 antibody | ELISA method |
| Example 3 | FIG. 5 | Plasma | VA64 | 1 | −80° C. | CD63 antibody | ELISA method |
| Example 3 | FIG. 5 | Plasma | VA64 | 3 | −80° C. | CD63 antibody | ELISA method |
| Comparative Example 3 | FIG. 2 | COLO201 cell culture supernatant | — | 1 | −80° C. | CD63 antibody | ELISA method |
| Comparative Example 3 | FIG. 2 | COLO201 cell culture supernatant | — | 3 | −80° C. | CD63 antibody | ELISA method |
| Comparative Example 3 | FIG. 3 | Mesenchymal stem cell culture supernatant | — | 1 | −80° C. | CD81 antibody | ELISA method |
| Comparative Example 3 | FIG. 3 | Mesenchymal stem cell culture supernatant | — | 3 | −80° C. | CD81 antibody | ELISA method |
| Comparative Example 3 | FIG. 4 | Serum | — | 1 | −80° C. | CD63 antibody | ELISA method |
| Comparative Example 3 | FIG. 4 | Serum | — | 3 | −80° C. | CD63 antibody | ELISA method |
| Comparative Example 3 | FIG. 5 | Plasma | — | 1 | −80° C. | CD63 antibody | ELISA method |
| Comparative Example 3 | FIG. 5 | Plasma | — | 3 | −80° C. | CD63 antibody | ELISA method |
| Example 4 | FIG. 6 | COLO201 cell culture supernatant | VA64 | 1 | −80° C. | CD9 antibody | ELISA method |
| Example 4 | FIG. 6 | COLO201 cell culture supernatant | VA64 | 5 | −80° C. | CD antibody | ELISA method |

TABLE 1-continued

| Number of Example/ Comparative Example | Figure | Specimen | Polymer or Trehalose | Number of times of freezing and thawing operation | Freezing temperature | Antibody used for detection | Experimental method |
|---|---|---|---|---|---|---|---|
| Example 4 | FIG. 6 | COLO201 cell culture supernatant | VA64 | 1 | −80° C. | CD63 antibody | ELISA method |
| Example 4 | FIG. 6 | COLO201 cell culture supernatant | VA64 | 5 | −80° C. | CD63 antibody | ELISA method |
| Example 4 | FIG. 7 | COLO201 cell culture supernatant | VA64 | 1 | −20° C. | CD9 antibody | ELISA method |
| Example 4 | FIG. 7 | COLO201 cell culture supernatant | VA64 | 5 | −20° C. | CD9 antibody | ELISA method |
| Example 4 | FIG. 7 | COLO201 cell culture supernatant | VA64 | 1 | −20° C. | CD63 antibody | ELISA method |
| Example 4 | FIG. 8 | COLO201 cell culture supernatant | VA64 | 5 | −20° C. | CD63 antibody | ELISA method |
| Example 5 | FIG. 8 | COLO201 cell culture supernatant | VA64 | 15 | −20° C. | CD9 antibody | ELISA method |
| Example 5 | FIG. 8 | COLO201 cell culture supernatant | VA64 | 15 | −20° C. | CD63 antibody | ELISA method |
| Example 5 | FIG. 8 | COLO201 cell culture supernatant | VA64 | 15 | −20° C. | CD81 antibody | ELISA method |
| Example 6 | FIG. 9 | COLO201 cell culture supernatant | VA64 | 15 | −20° C. | — | Electron microscopic observation |
| Comparative Example 4 | FIG. 10 | COLO201 cell culture supernatant | Trehalose | 3 | −80° C. | CD9 antibody | ELISA method |
| Comparative Example 5 | FIG. 10 | COLO201 cell culture supernatant | — | 3 | −80° C. | CD9 antibody | ELISA method |
| Example 7 | FIG. 11 | COLO201 cell culture supernatant | 17PF | 1 | −80° C. | CD9 antibody | ELISA method |
| Example 7 | FIG. 11 | COLO201 cell culture supernatant | 17PF | 3 | −80° C. | CD9 antibody | ELISA method |
| Example 8 | FIG. 11 | COLO201 cell culture supernatant | 12PF | 1 | −80° C. | CD9 antibody | ELISA method |
| Example 8 | FIG. 11 | COLO201 cell culture supernatant | 12PF | 3 | −80° C. | CD9 antibody | ELISA method |
| Comparative Example 6 | FIG. 11 | COLO201 cell culture supernatant | — | 1 | −80° C. | CD9 antibody | ELISA method |
| Comparative Example 6 | FIG.11 | COLO201 cell culture supernatant | — | 3 | −80° C. | CD9 antibody | ELISA method |

\* In the table, VA64 indicates Kollidon (trade name) VA64, 17PF indicates Kollidon (trade name) 17PF, and 12PF indicates Kollidon (trade name) 12PF. Kollidon (trade name) VA64 is a copolymer that contains a monomer unit derived from vinylpyrrolidone and a monomer unit derived from vinyl acetate, and Kollidon (trade name) 17PF and Kollidon (trade name) 12PF are vinylpyrrolidone.

Example 8: Exosome Storage Stabilization Test

The storage stabilization effect of Kollidon (registered trade name) VA64 exosomes in the cryopreservation an exosome was verified with a proteome analysis.

(1) Acquisition of Exosome

Exosomes were purified from the culture supernatant of the COLO201 cell by the same method as in Example 1 to obtain a purified exosome solution.

(2) Exosome Cryopreservation

The obtained purified exosome solution was incubated at 4° C. for 16 hours. Next, a 5% (w/v) Kollidon aqueous solution (Kollidon (registered trade name) VA64 (manufactured by BASF SE) and Otsuka Distilled Water (manufactured by Otsuka Pharmaceutical Co., Ltd.) were prepared. A 5% (w/v) Kollidon aqueous solution was added to the purified exosome solution after incubation to a final concentration of 0.05% (w/v). The obtained solution was frozen at −80° C. for 8 days and then thawed at room temperature for 10 minutes.

(3) Verification of Storage Stabilization Effect

The solution after freezing and thawing was subjected to a protein precipitation treatment with acetone, followed by further washing with acetone. Then, a hydrolysis treatment with trypsin was carried out, followed by LC-MS/MS. Peptides and proteins were identified by sequence database search based on the data extracted from MS/MS.

(4) Result

The number of identified peptides and the number of identified proteins are shown in Table 2 below. In the table, VA64 indicates Kollidon (registered trade name) VA64. "VA64 added" indicates the result of Example 8.

TABLE 2

| Specimen name | Number of identified peptides | Number of identified proteins |
| --- | --- | --- |
| VA64 added | 11166 | 1522 |
| VA64 not added | 7142 | 1194 |

Comparative Example 7: Effect of Freezing and Thawing on Storage Stabilization of Exosome Proteome analysis was carried out in the same manner as in Example 8 except that the 5% (w/v) Kollidon aqueous solution was not added to the purified exosome solution after incubation, and then peptides and proteins contained in the solution after freezing and thawing were identified.

The number of identified peptides and the number of identified proteins are shown in Table 2. "VA64 not-added" indicates the result of Comparative Example 7.

From Table 2, it has been shown that in a case (Example 8) where the exosome is subjected to freezing and thawing using Kollidon (registered trade name) VA64, the number of peptides and the number of proteins is large as compared with a case (Comparative Example 7) where only the exosome solution was subjected to freezing and thawing.

From these results, it has been found that using the polymer having a monomer unit derived from vinylpyrrolidone, it is possible to stably store proteins and peptides contained in an extracellular vesicle in a case where the extracellular vesicle is cryopreserved.

The invention claimed is:

1. A storage stabilization method for an extracellular vesicle, comprising cryopreserving an extracellular vesicle in a presence of a polymer having a monomer unit derived from vinylpyrrolidone,
    wherein the polymer is a copolymer containing a monomer unit derived from vinylpyrrolidone and a monomer unit derived from vinyl acetate, or polyvinylpyrrolidone having a weight-average molecular weight of 1,500 to 15,000;
    the cryopreserving of an extracellular vesicle is cryopreserving a storage solution comprising the polymer, the extracellular vesicle, and an aqueous solution; and
    the concentration of the polymer in the storage solution is 0.001 to 1% (w/v).

2. The storage stabilization method for an extracellular vesicle according to claim 1, wherein the polymer is a copolymer containing a monomer unit derived from vinylpyrrolidone and a monomer unit derived from vinyl acetate.

3. The storage stabilization method for an extracellular vesicle according to claim 2, wherein a constitution ratio of the monomer unit derived from vinylpyrrolidone to the monomer unit derived from vinyl acetate in the copolymer is 1:0.1 to 1:3.

4. The storage stabilization method for an extracellular vesicle according to claim 2, wherein a Fikentscher K value of the copolymer is 5 to 50.

5. The storage stabilization method for an extracellular vesicle according to claim 2, wherein a weight-average molecular weight of the copolymer is 3,000 to 250,000.

6. The storage stabilization method for an extracellular vesicle according to claim 1, wherein the polymer is polyvinylpyrrolidone.

7. The storage stabilization method for an extracellular vesicle according to claim 6, wherein a Fikentscher K value of the polyvinylpyrrolidone is 9 to 20.

8. The storage stabilization method for an extracellular vesicle according to claim 1, wherein the extracellular vesicle is an isolated extracellular vesicle.

9. The storage stabilization method for an extracellular vesicle according to claim 1, which further comprises isolating an extracellular vesicle from a biological specimen prior to cryopreserving the extracellular vesicle.

\* \* \* \* \*